(12) United States Patent
D'Agostino et al.

(10) Patent No.: US 9,675,341 B2
(45) Date of Patent: Jun. 13, 2017

(54) EMERGENCY SELF-RETAINING SUTURES AND PACKAGING

(75) Inventors: William L. D'Agostino, Hamden, CT (US); Matt Merkel, Birdsboro, PA (US); Ron Bowser, Shoemakersville, PA (US); Mark Hoyt, Birdsboro, PA (US)

(73) Assignee: Ethicon Inc., Somerville, NJ (US)

( * ) Notice: Subject to any disclaimer, the term of this patent is extended or adjusted under 35 U.S.C. 154(b) by 579 days.

(21) Appl. No.: 13/882,841

(22) PCT Filed: Nov. 9, 2011

(86) PCT No.: PCT/US2011/060069
§ 371 (c)(1),
(2), (4) Date: May 1, 2013

(87) PCT Pub. No.: WO2012/064902
PCT Pub. Date: May 18, 2012

(65) Prior Publication Data
US 2013/0226233 A1 Aug. 29, 2013

Related U.S. Application Data

(60) Provisional application No. 61/411,918, filed on Nov. 9, 2010, provisional application No. 61/412,389, filed on Nov. 10, 2010.

(51) Int. Cl.
*A61B 17/04* (2006.01)
*A61B 17/06* (2006.01)
(Continued)

(52) U.S. Cl.
CPC ........ *A61B 17/06166* (2013.01); *A61B 17/04* (2013.01); *A61B 17/06138* (2013.01); *A61B 50/30* (2016.02); *A61B 90/92* (2016.02); *A61B 2017/0472* (2013.01); *A61B 2017/0479* (2013.01); *A61B 2017/06052* (2013.01);
(Continued)

(58) Field of Classification Search
CPC .......... A61B 17/06166; A61B 17/0401; A61B 2017/06176
See application file for complete search history.

(56) References Cited

U.S. PATENT DOCUMENTS

| | | |
|---|---|---|
| 709,392 A | 9/1902 | Brown |
| 733,723 A | 7/1903 | Lukens |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

US 8,663,276, 03/2014, Leung et al. (withdrawn)
(Continued)

*Primary Examiner* — Ashley Fishback

(57) ABSTRACT

A removable self-retaining suture system and methods for use thereof in emergency situations. The system comprises one or more self-retaining suture segments and a grasp engagement element. The system may be used for temporary wound closure in a trauma victim, and may be easily removed upon the availability of proper medical care to the victim.

12 Claims, 15 Drawing Sheets

(51) Int. Cl.
  *A61B 50/30* (2016.01)
  *A61B 90/92* (2016.01)
(52) U.S. Cl.
  CPC .............. *A61B 2017/06057* (2013.01); *A61B 2017/06176* (2013.01)

(56) References Cited

U.S. PATENT DOCUMENTS

| | | |
|---|---|---|
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,591,063 A | 4/1952 | Goldberg |
| 2,647,625 A | 8/1953 | Mason et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,830,366 A | 4/1958 | Chisena |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,082,523 A | 3/1963 | Modes et al. |
| 3,123,077 A | 3/1964 | Alcamo |
| 3,136,418 A | 6/1964 | Stacy et al. |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,749,238 A | 7/1973 | Taylor |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal |
| 4,008,303 A | 2/1977 | Glick et al. |
| 4,014,434 A | 3/1977 | Thyen |
| 4,024,871 A | 5/1977 | Stephenson |
| 4,027,608 A | 6/1977 | Arbuckle |
| 4,043,344 A | 8/1977 | Landi |
| 4,052,988 A | 10/1977 | Doddi et al. |
| 4,063,638 A | 12/1977 | Marwood |
| D246,911 S | 1/1978 | Bess, Jr. et al. |
| 4,069,825 A | 1/1978 | Akiyama |
| 4,073,298 A | 2/1978 | Le Roy |
| 4,075,962 A | 2/1978 | Mabry |
| 4,098,210 A | 7/1978 | Wright |
| 4,135,623 A | 1/1979 | Thyen |
| 4,137,921 A | 2/1979 | Okuzumi et al. |
| 4,182,340 A | 1/1980 | Spencer |
| 4,183,431 A | 1/1980 | Schmidt et al. |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,253,563 A | 3/1981 | Komarnycky |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Putz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,496,045 A | 1/1985 | Ferguson et al. |
| 4,505,274 A | 3/1985 | Speelman |
| 4,510,934 A | 4/1985 | Batra |
| 4,524,771 A | 6/1985 | Troutman et al. |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |

(56) References Cited

U.S. PATENT DOCUMENTS

| | | |
|---|---|---|
| 4,712,553 A | 12/1987 | MacGregor |
| 4,719,917 A | 1/1988 | Barrows et al. |
| 4,741,330 A | 5/1988 | Hayhurst |
| 4,750,910 A | 6/1988 | Takayanagi et al. |
| 4,776,337 A | 10/1988 | Palmaz |
| 4,813,537 A | 3/1989 | Okuhara et al. |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,043 A | 8/1990 | Roshdy et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,059,207 A | 10/1991 | Shah |
| 5,084,063 A | 1/1992 | Korthoff |
| 5,089,010 A | 2/1992 | Korthoff |
| 5,089,012 A | 2/1992 | Prou |
| 5,099,994 A | 3/1992 | Kalinski et al. |
| 5,101,968 A | 4/1992 | Henderson et al. |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,121,836 A | 6/1992 | Brown et al. |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,131,534 A | 7/1992 | Brown et al. |
| 5,133,738 A | 7/1992 | Korthoff et al. |
| 5,141,520 A | 8/1992 | Goble et al. |
| 5,147,382 A | 9/1992 | Gertzman et al. |
| 5,154,283 A | 10/1992 | Brown |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green et al. |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,386,912 A | 2/1995 | Holzwarth et al. |
| 5,387,383 A | 2/1995 | Collier et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,362 A | 8/1995 | Sinn |
| 5,437,680 A | 8/1995 | Yoon et al. |
| 5,450,860 A | 9/1995 | O'Connor |
| 5,451,461 A | 9/1995 | Broyer |
| 5,460,263 A | 10/1995 | Brown et al. |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,503,266 A | 4/1996 | Kalbfeld et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,611 A | 7/1996 | Bordighon et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,821 A | 10/1996 | Brown et al. |
| 5,566,822 A | 10/1996 | Scanlon |
| 5,569,272 A | 10/1996 | Reed et al. |

(56) References Cited

U.S. PATENT DOCUMENTS

| | | |
|---|---|---|
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,715,942 A | 2/1998 | Li et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,871,089 A | 2/1999 | Odermatt |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,918,733 A | 7/1999 | Cerwin et al. |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,042 A | 1/2000 | Cerwin et al. |
| 6,015,410 A | 1/2000 | Tormala et al. |
| 6,024,757 A | 2/2000 | Haase et al. |
| 6,027,523 A | 2/2000 | Schmieding |
| 6,029,806 A | 2/2000 | Cerwin et al. |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| 6,135,385 A | 10/2000 | Martinez de Lahidgalga |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,254,616 B1 | 7/2001 | Wright |
| 6,260,696 B1 | 7/2001 | Braginsky et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,481,569 B1 | 11/2002 | Alpern |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |

(56) References Cited

U.S. PATENT DOCUMENTS

| | | |
|---|---|---|
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,659,270 B2 | 12/2003 | Williamson, IV et al. |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,739,450 B2 | 5/2004 | Roshdy et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,938,755 B2 | 9/2005 | Braginsky et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,029,490 B2 | 4/2006 | Grafton et al. |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,513,904 B2 | 4/2009 | Sulamanidze et al. |
| 7,582,105 B2 | 9/2009 | Kolster |
| 7,600,634 B2 | 10/2009 | Malinowski et al. |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,246,652 B2 | 8/2012 | Ruff |
| 8,308,761 B2 | 11/2012 | Brailovski et al. |
| 8,403,947 B2 | 3/2013 | Ochiai |
| 8,460,338 B2 | 6/2013 | Goraltchouk et al. |
| 8,615,856 B1 | 12/2013 | Gelbart |
| 8,641,732 B1 | 2/2014 | Goraltchouk et al. |
| 8,783,258 B2 | 7/2014 | Jacobs et al. |
| 8,932,328 B2 | 1/2015 | Megaro et al. |
| 9,023,081 B2 | 5/2015 | Maiorino et al. |
| 9,038,688 B2 | 5/2015 | Maiorino et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0004579 A1 | 1/2003 | Rousseau et al. |
| 2003/0040795 A1 | 2/2003 | Elson et al. |
| 2003/0052028 A1 | 3/2003 | Lei |

(56) References Cited

U.S. PATENT DOCUMENTS

| | | |
|---|---|---|
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0050721 A1 | 3/2004 | Roby et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Yeung et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0116718 A1 | 6/2006 | Leiboff |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0187861 A1 | 8/2007 | Genova et al. |
| 2007/0208355 A1 | 9/2007 | Ruff |
| 2007/0208377 A1 | 9/2007 | Kaplan et al. |
| 2007/0213744 A1 | 9/2007 | Farris |
| 2007/0213770 A1 | 9/2007 | Drefyss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |

(56) References Cited

U.S. PATENT DOCUMENTS

| | | |
|---|---|---|
| 2007/0225764 A1 | 9/2007 | Benavitz et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0243228 A1 | 10/2007 | McKay et al. |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0128296 A1 | 6/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281355 A1 | 11/2008 | Mayer et al. |
| 2008/0281357 A1 | 11/2008 | Sung et al. |
| 2008/0300491 A1 | 12/2008 | Bonde et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1* | 9/2009 | Leung .............. A61B 17/06166 606/139 |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0312791 A1 | 12/2009 | Lindh, Sr. et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0160961 A1 | 6/2010 | Nawrocki et al. |
| 2010/0163056 A1 | 7/2010 | Tschopp et al. |
| 2010/0170812 A1 | 7/2010 | Odierno |
| 2010/0198257 A1 | 8/2010 | Stopek et al. |
| 2010/0211097 A1 | 8/2010 | Hadba et al. |
| 2010/0211098 A1 | 8/2010 | Hadba et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0056859 A1 | 3/2011 | Kozlowski |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0251640 A1 | 10/2011 | Lauria |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0109188 A1 | 5/2012 | Viola |
| 2012/0116449 A1 | 5/2012 | Kirsch et al. |
| 2012/0245659 A1 | 9/2012 | Matthews |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226233 A1 | 8/2013 | D'Agostino et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |
| 2013/0345745 A1 | 12/2013 | Kim |
| 2014/0039527 A1 | 2/2014 | Avelar et al. |

FOREIGN PATENT DOCUMENTS

| | | | |
|---|---|---|---|
| CA | WO 2009132284 A2 * | 10/2009 | ....... A61B 17/06166 |
| CN | 2640420 | 9/2004 | |
| DE | 01810800 | 6/1970 | |
| DE | 02618662 | 11/1977 | |

(56) References Cited

FOREIGN PATENT DOCUMENTS

| | | |
|---|---|---|
| DE | 03227984 | 2/1984 |
| DE | 04302895 | 8/1994 |
| DE | 19618891 | 4/1997 |
| DE | 19802213 | 8/1999 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0726062 | 8/1996 |
| EP | 0576337 A1 | 3/1997 |
| EP | 0576337 B1 | 3/1997 |
| EP | 0760228 | 3/1997 |
| EP | 0574707 | 8/1997 |
| EP | 0612504 | 11/1997 |
| EP | 0558993 | 4/1998 |
| EP | 0913123 | 5/1999 |
| EP | 0914802 | 5/1999 |
| EP | 0916310 | 5/1999 |
| EP | 0664198 | 6/1999 |
| EP | 0960600 | 12/1999 |
| EP | 0717958 | 8/2000 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 1852071 | 11/2007 |
| EP | 2036502 | 3/2009 |
| EP | 1948261 | 11/2010 |
| EP | 2245992 | 11/2010 |
| EP | 1726317 | 7/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 47-044390 | 11/1972 |
| JP | 1506362 | 4/1978 |
| JP | 54-116419 | 9/1979 |
| JP | 63-288146 | 11/1988 |
| JP | 64-013034 | 1/1989 |
| JP | 001113091 | 5/1989 |
| JP | 3-080868 | 4/1991 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2007-502281 | 2/2007 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 560599 | 6/1977 |
| SU | 1745214 | 7/1992 |
| SU | 1752358 | 8/1992 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 96/06565 | 3/1996 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/003925 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/008815 | 1/2010 |
| WO | WO 2010/052007 | 5/2010 |
| WO | WO 2011/025760 | 3/2011 |
| WO | WO 2011/053375 | 5/2011 |
| WO | WO 2011/090628 | 7/2011 |
| WO | WO 2011/139916 | 11/2011 |

(56) References Cited

FOREIGN PATENT DOCUMENTS

| WO | WO 2011/140283 | 11/2011 |
|---|---|---|
| WO | WO 2015/069042 | 5/2015 |

OTHER PUBLICATIONS

Extended European Search Report re: 11839516 dated Aug. 14, 2014.
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED—University of Puerto Rico, Mayaguez May 2005, p. F1-F27.
Delorenzi, C.L., "Barbed Sutures: Rationale and Technique", Aesthetic Surg. J. Mar. 2006 26(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 2006 27(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), an Investigation of Micro Structures, Sensors, Actuators, Machines and Robots pp. 253-258.

Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, the Next Generation Oct. 17-19, 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(Σ-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.

(56) References Cited

OTHER PUBLICATIONS

Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Muliner, "Metal Foam Has a Good Memory", Dec. 18, 2007 Original story at <http.//www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (APTOS Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan E.L. et al., "A wireless, passive strain sensor based on the harmonic response of magnetically soft materials", Smart Materials and Structures 17 (2008): pp. 1-6.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
International Search Report and Written Opinion for PCT/US2011/060069 dated May 18, 2012.
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.

(56) References Cited

OTHER PUBLICATIONS

European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/064921 dated Nov. 19, 2008, 3 pages.
International Search Report for PCT/US2008/075849 dated Jun. 23, 2009, 19 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2012/030441 dated Sep. 27, 2012.
International Search Report for PCT/US2012/041001 dated Sep. 26, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.
Written Opinion of the International Searching Authority re: PCT/US2010/056898 dated Aug. 2, 2011.
Written Opinion of the International Searching Authority re: PCT/US2012/041001 dated Sep. 26, 2012.
Croce, E. et al 'Intracorporeal Knot-Tying and Suturing Techniques in Laparoscopic Survery: Technical Details' Journal of the Society of Laparoendoscopic Surgeons (2000) vol. 4 pp. 17-22.
Jeong, H.E. et al 'A nontransferring dry adhesive with hierarchial polymer nanohairs' PNAS 106 (14) pp. 5639-5644 (2009).

* cited by examiner

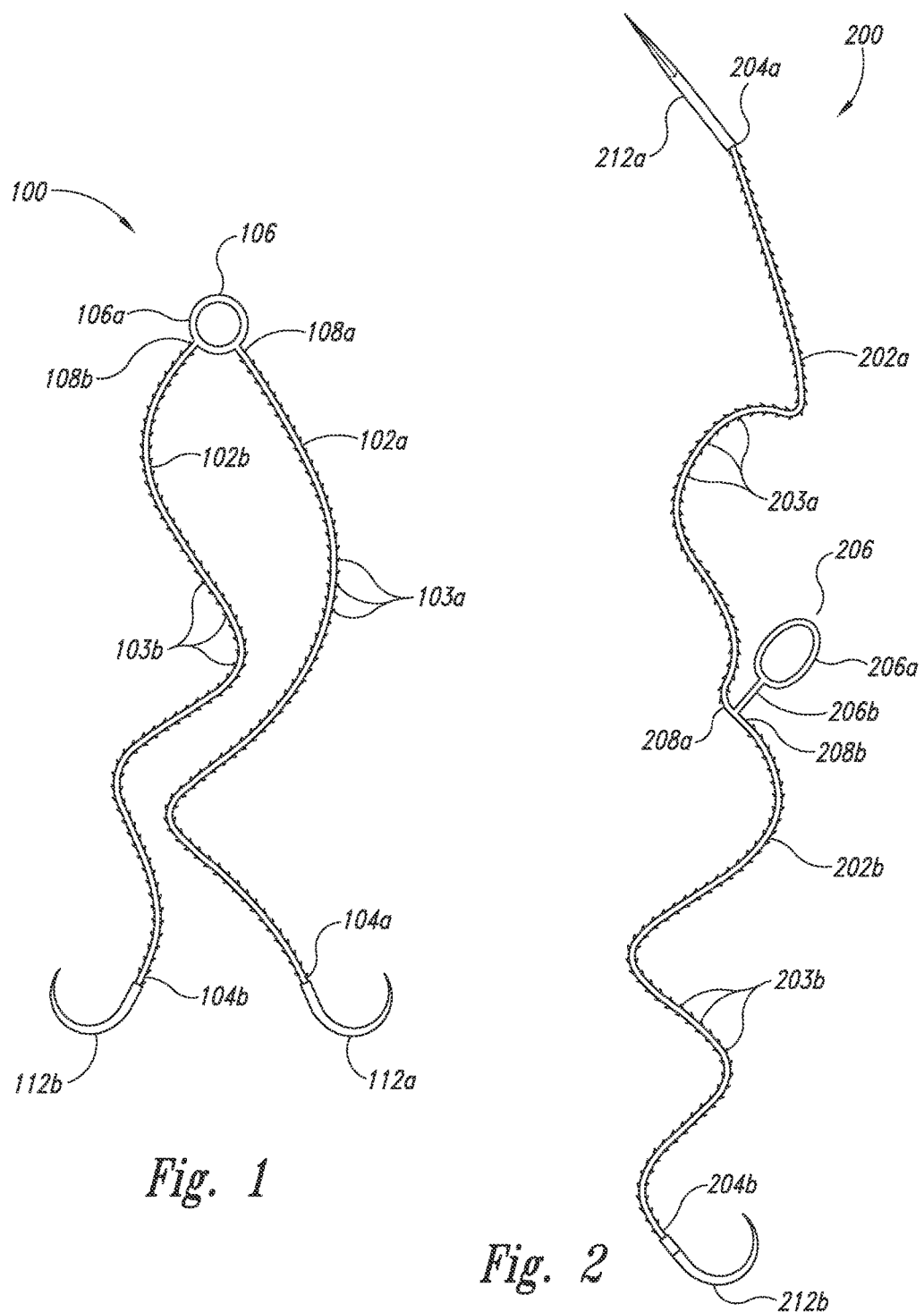

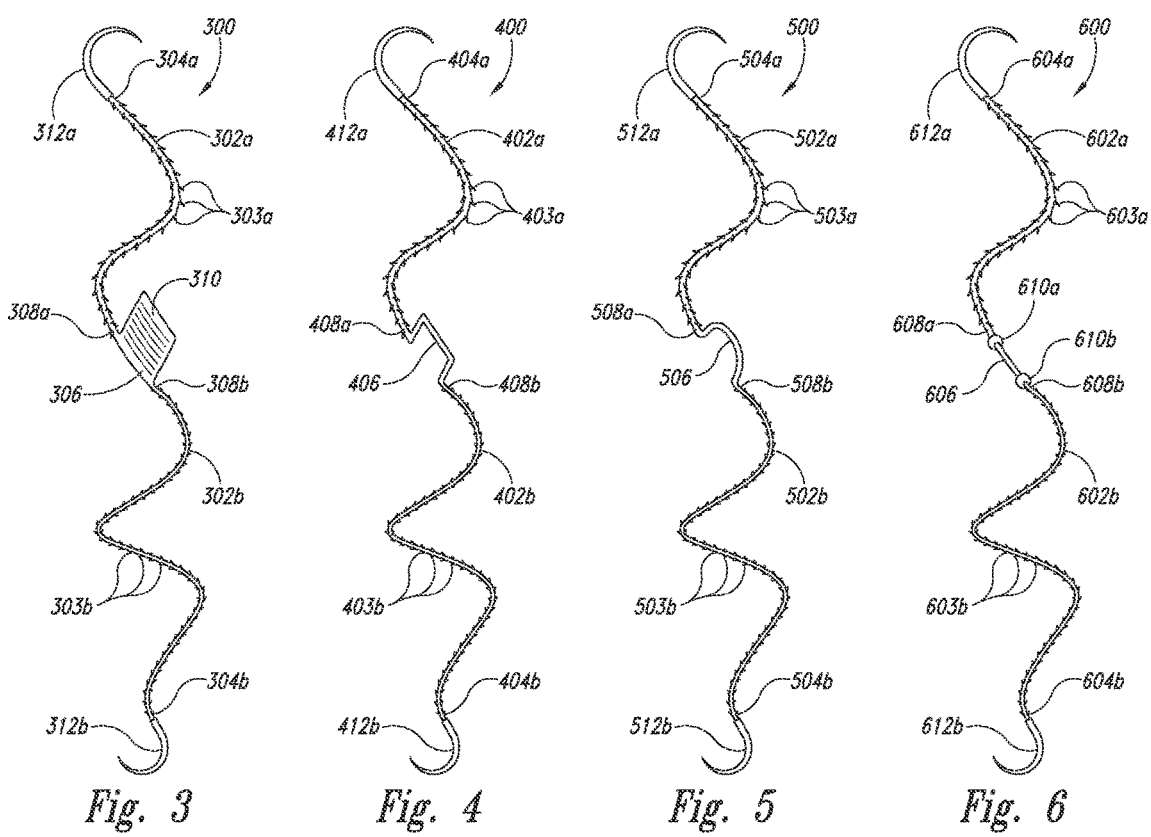

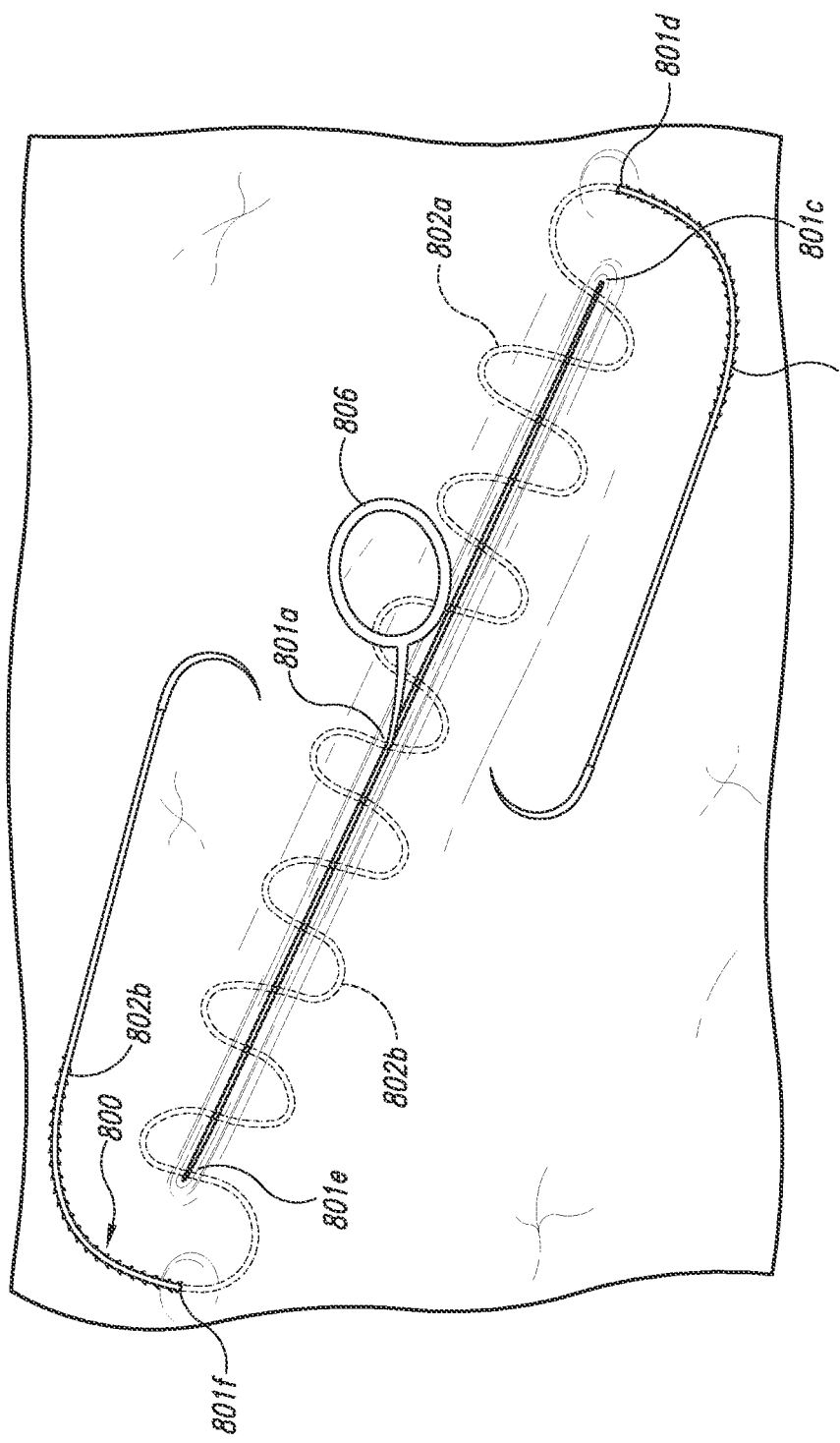

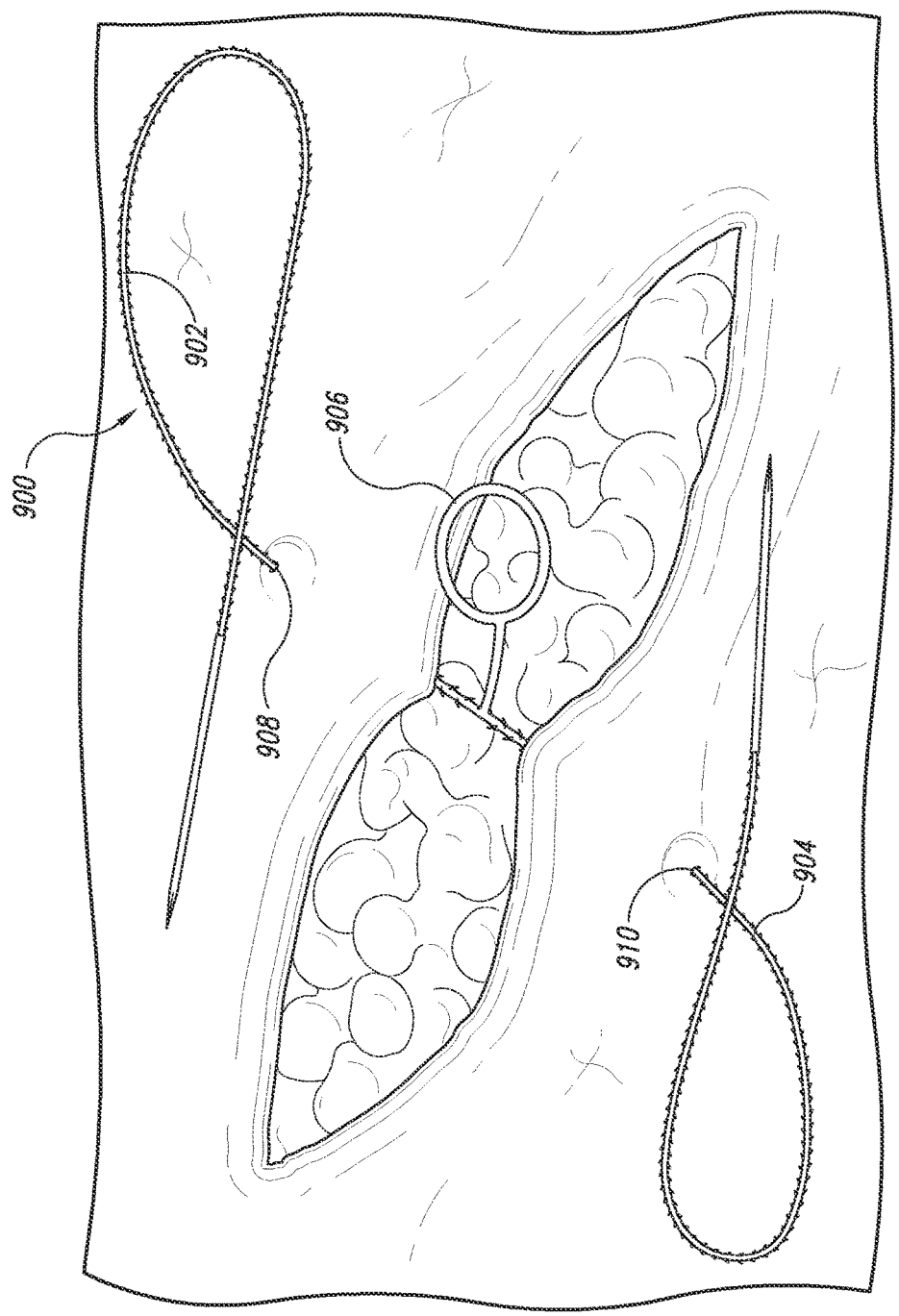

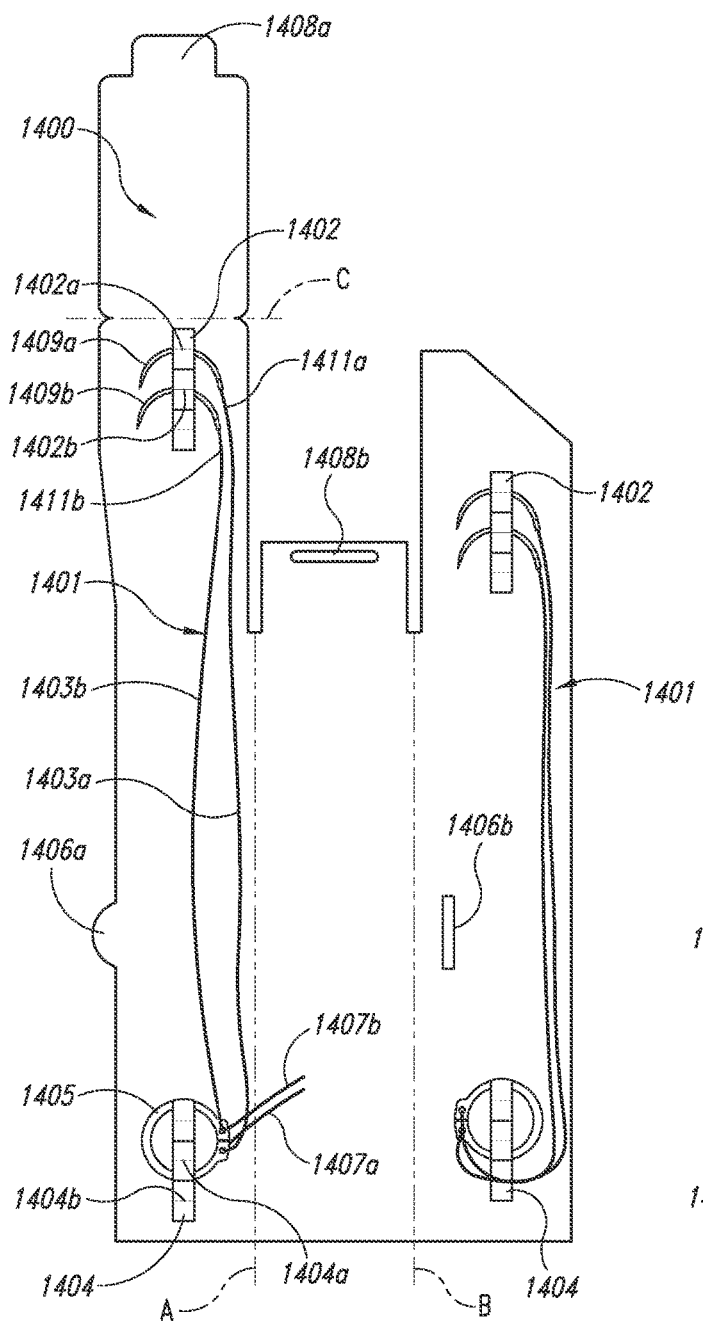
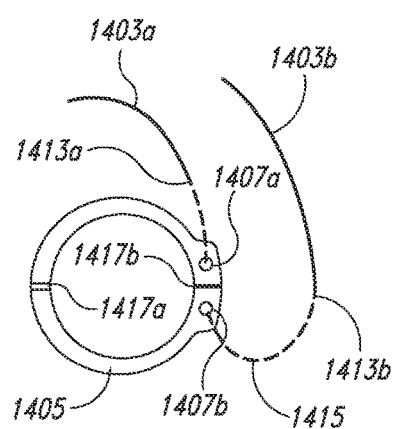
Fig. 14A
Fig. 14B

EMERGENCY SELF-RETAINING SUTURES AND PACKAGING

CROSS-REFERENCE TO RELATED APPLICATIONS

This application is the national stage of international application number PCT/US2011/060069, filed Nov. 9, 2011, which is incorporated herein by reference in its entirety and which claims the benefit under 35 U.S.C. §119(e) of U.S. Provisional Patent Application No. 61/411,918 filed Nov. 9, 2010, and U.S. Provisional Patent Application No. 61/412,389, filed Nov. 10, 2010, which provisional applications are incorporated herein by reference in their entireties.

FIELD OF INVENTION

The present invention relates generally to filaments for surgical procedures, methods of manufacturing filaments for surgical procedures, and uses thereof.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available, and the shape, and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

The advantages of greater accuracy and time savings provided by self-retaining sutures may be more pronounced when surgical conditions are sub-optimal. In areas of armed conflict, natural disaster zones, sites of terrorist attack, and other emergency situations, wound closure (and other tissue approximation) may be more quickly, easily, and effectively accomplished with self-retaining sutures than with their conventional counterparts and thus could potentially save more lives. Obviating the need for knots would not only enable a first responder to more quickly close a wound, but would also allow a nurse, surgeon, or other medical trauma staff to more quickly remove the temporary or emergency closure in order to treat the trauma victim.

For example, to treat soldiers suffering traumatic injuries on a battlefield, a military medic must rapidly close external wounds and quickly transport the injured patient to the closest field hospital. Then, at the field hospital, the medical personnel must remove the sutures from the wound and begin surgery. The knotless wound closure made possible by self-retaining sutures provides a significant advantage for rapid closure in the field. Likewise, self-retaining sutures can be easily and quickly removed from tissue, by locating the transition segment of a bidirectional suture, severing it, and then pulling out the remaining suture segments by each segment's distal, or deployment, ends. (Similarly, in the case of a unidirectional suture, the anchor may be severed and the suture segment pulled out from the tissue by its deployment end.) Given the time constraints presented by the aftermath of battle, in which multiple trauma victims would be brought in for treatment at once, in sometimes sub-optimal surgical conditions, as well as the potentially complex nature of wounds sustained by those injured in combat, the rapid identification of the self-retaining suture's transition point in a wound closure can be difficult.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and 6,241,747). Although any number of sequential or intermittent configurations of retainers are possible, a common form of bidirectional self-retaining suture involves a needle at one end of a suture thread which has barbs having tips projecting "away" from the suture deployment end (which may be sharp enough to penetrate tissue itself or may have a needle attached to it) until the transition portion of the suture is reached; at the transition portion the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb may be pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

BRIEF SUMMARY OF INVENTION

Given the advantages of self-retaining sutures, it is desired to provide improved self-retaining sutures and methods useful in emergency situations, for wound closure and tissue approximation in suboptimal surgical conditions, such as in areas of armed conflict and natural disaster.

In accordance with one aspect, the present invention provides bidirectional self-retaining sutures having grasp engagement elements to facilitate suture deployment and subsequent removal.

In accordance with another aspect, the present invention provides unidirectional self-retaining sutures having grasp engagement elements to facilitate suture deployment and subsequent removal.

In accordance with another aspect, the present invention provides multidirectional self-retaining sutures having grasp engagement elements to facilitate suture deployment and subsequent removal.

In accordance with another aspect, the present invention provides methods of deploying and subsequently removing self-retaining sutures having grasp engagement elements.

In accordance with another aspect, the present invention provides self-retaining sutures having detachable grasp engagement elements.

The following are exemplary embodiments of the present invention:

Embodiment 1

A removable bidirectional self-retaining suture, the suture comprising:
a. a first end, a second end, and a periphery;
b. a plurality of retainers, the retainers on a first portion of the suture between the first end of the suture and a first axial location on the suture for permitting movement of the suture through tissue in a direction of movement of the first end and preventing movement of the suture through tissue in a direction opposite the direction of movement of the first end, and the retainers on a second portion of the suture between the second end of the suture and a second axial location on the suture permitting movement of the suture through tissue in a direction of movement of the second end and preventing movement of the suture through tissue in a direction opposite the direction of movement of the second end; and
c. a grasp engagement element between the first and second axial locations.

Embodiment 2

The suture of embodiment 1, wherein the grasp engagement element comprises a loop.

Embodiment 3

The suture of embodiment 2, wherein the loop is discontinuous.

Embodiment 4

The suture of embodiment 1, wherein the grasp engagement element comprises a tab.

Embodiment 5

The suture of embodiment 1, wherein the grasp engagement element comprises a suture segment having a stop at each end thereof, for preventing entry of said suture segment into tissue.

Embodiment 6

The suture of embodiment 1, wherein the grasp engagement element is comprises a different colour than the rest of the suture.

Embodiment 7

The suture of embodiment 6, wherein the suture further comprises a frangible portion between the grasp engagement element and the first and second axial locations for facilitating removal of the grasp engagement element from the suture.

Embodiment 8

The suture of embodiment 6, wherein the grasp engagement element further comprises an enhanced gripping surface.

Embodiment 9

The suture of embodiment 1, wherein the grasp engagement element has a periphery greater than the periphery of the suture.

Embodiment 10

The suture of embodiment 9, wherein the suture further comprises a frangible portion between the grasp engagement element and the first and second axial locations for facilitating removal of the grasp engagement element from the suture.

Embodiment 11

The suture of embodiment 9, wherein the grasp engagement element further comprises an enhanced gripping surface.

Embodiment 12

The suture of embodiment 1, wherein the grasp engagement element further comprises an enhanced gripping surface.

Embodiment 13

The suture of embodiment 1, wherein the suture further comprises a frangible portion between the grasp engagement element and the first and second axial locations for facilitating removal of the grasp engagement element from the suture.

Embodiment 14

The suture of embodiment 1, further comprising a detachable connector connecting the grasp engagement element and the suture.

Embodiment 15

The suture of embodiment 1, wherein the grasp engagement element is at least in part flexible.

Embodiment 16

The suture of embodiment 1, wherein the grasp engagement element is at least in part rigid.

Embodiment 17

The suture of embodiment 1, wherein the grasp engagement element comprises a different material than the rest of the suture.

Embodiment 18

The suture of embodiment 2, wherein the configuration of the loop is selected from the class comprising circles, ellipses, and polygons.

Embodiment 19

A removable multidirectional self-retaining system comprising:
a. a grasp engagement element;
b. at least three suture segments, each suture segment having a plurality of retainers between a first end of the suture segment and a second end of the suture segment for permitting movement of the suture through tissue in a direction of movement of the first end and preventing movement of the suture segment through tissue in a direction opposite the direction of movement of the first end, and a second end of each suture segment being attached to the grasp engagement element.

Embodiment 20

The system of embodiment 19, wherein the grasp engagement element comprises a loop.

Embodiment 21

The system of embodiment 20, wherein the loop is discontinuous.

Embodiment 22

The system of embodiment 19, wherein the grasp engagement element comprises a tab.

Embodiment 23

The system of embodiment 19, wherein the grasp engagement element comprises a suture segment having a stop at each end thereof, for preventing entry of said suture segment into tissue.

Embodiment 24

The system of embodiment 20, wherein the loop is circular.

Embodiment 25

The system of embodiment 20, wherein the loop is elliptical.

Embodiment 26

The system of embodiment 20, wherein the loop is polygonal.

Embodiment 27

A method of emergency wound closure, comprising:
a. providing a bidirectional self-retaining suture having a plurality of retainers, the retainers on a first portion of the suture between a first end of the suture and a first axial location on the suture for permitting movement of the suture through tissue in a direction of movement of the first end and preventing movement of the suture through tissue in a direction opposite the direction of movement of the first end, and the retainers on a second portion of the suture between a second end of the suture and a second axial location on the suture permitting movement of the suture through tissue in a direction of movement of the second end and preventing movement of the suture through tissue in a direction opposite the direction of movement of the second end;
b. inserting the first end of the suture into tissue at a first insertion point between first and second ends of the wound;
c. drawing the first end of the suture towards the first end of the wound along a first deployment path through tissue on alternating sides of the wound to a first exit point;
d. inserting the second end of the suture into tissue at a second insertion point between the first and second ends of the wound, leaving a portion of the suture between the first and second insertion points;
e. drawing the second end of the suture towards the second end of the wound along a second deployment path through tissue on alternating sides of the wound to a second exit point; and,
f. severing the suture along the portion between the first and second insertion points for removal of the suture from the wound prior to provision of permanent treatment.

Embodiment 28

The method of embodiment 27, wherein the step of inserting the second end of the suture into tissue is performed before the step of drawing the first end of the suture towards the first end of the wound.

Embodiment 29

A method of emergency wound closure, comprising:
a. providing a unidirectional self-retaining suture, the suture having a plurality of retainers between a first and second end of the suture for permitting movement of the suture through tissue in a direction of movement of the first end and preventing movement of the suture through tissue in a direction opposite the direction of movement of the first end, and a grasp engagement element at the second end of the suture;
b. positioning the grasp engagement element at least in part outside the wound;
c. inserting the first end of the suture into tissue at an insertion point at the wound; and,
d. drawing the first end of the suture towards an end of the wound along a deployment path through tissue on alternating sides of the wound to an exit point outside the tissue.

Embodiment 30

The method of embodiment 29, wherein the unidirectional suture further comprises a frangible portion proximal to the grasp engagement element.

Embodiment 31

A method of emergency wound closure comprising:
a. providing a multidirectional self-retaining system, the system having a grasp engagement element and at least two suture segments, each suture segment having a plurality of retainers between a first end of the suture segment and a second end of the suture segment for permitting movement of the suture through tissue in a direction of movement of the first end and preventing movement of the suture segment through tissue in a direction opposite the direction of movement of the first end, and a second end of each suture segment being attached to the grasp engagement element;
b. positioning the grasp engagement element at least in part outside the wound;
c. inserting the first end of a first suture segment into tissue at a first insertion point at the wound;
d. drawing the first end of the first suture segment towards a first end of the wound along a first deployment path through tissue on alternating sides of the wound to a first exit point;
e. inserting the first end of a second suture segment into tissue at a second insertion point proximal to the first insertion point; and,
f. drawing the first end of the second suture segment towards a second end of the wound along a second deployment path through tissue on alternating sides of the wound to a second exit point.

Embodiment 32

The method of embodiment 31, wherein the self-retaining system comprises at least a third suture segment having a plurality of retainers between a first end of the suture segment and a second end of the suture segment for permitting movement of the suture through tissue in a direction of movement of the first end and preventing movement of the suture segment through tissue in a direction opposite the direction of movement of the first end, the second end of the third suture segment being attached to the grasp engagement element.

Embodiment 33

The method of embodiment 32, further comprising inserting the first end of the third suture segment into tissue at a third insertion point proximal to at least one of the first and second insertion points, and drawing the first end of the third suture segment towards a third end of the wound along a third deployment path through tissue on alternating sides of the wound to a third exit point.

Embodiment 34

The method of embodiment 312, wherein the grasp engagement element comprises a connection between the suture segments.

Embodiment 35

A method of achieving an emergency closure of a stellate wound having at least three tissue apexes, comprising:
a. providing a multidirectional self-retaining system, the system having a grasp engagement element and at least three suture segments, each suture segment having a plurality of retainers between a first end of the suture segment and a second end of the suture segment for permitting movement of the suture through tissue in a direction of movement of the first end and preventing movement of the suture segment through tissue in a direction opposite the direction of movement of the first end, and a second end of each suture segment being attached to the grasp engagement element;
b. positioning the grasp engagement element proximal to the tissue apexes;
c. inserting the first end of a first suture segment into a first tissue apex and drawing the first end of the first suture segment out of the tissue;
d. inserting the first end of a second suture segment into a second tissue apex and drawing the first end of the second suture segment out of the tissue; and,
e. inserting the first end of a third suture segment into tissue at a third tissue apex and drawing the first end of the third suture segment out of the tissue.

Embodiment 36

A method of removing an emergency self-retaining suture from tissue, the suture having a at least one self-retaining suture segment, the suture segment having a first end connected to grasp engagement element and a second end, the method comprising:
a. severing the grasp engagement element from the suture segment; and,
b. drawing the suture segment out of the tissue by its second end.

Embodiment 37

A package for holding a suture device having a grasp engagement element attached to at least one suture segment having a distal end, the package comprising
a. a base having at least one surface; and,
b. a segment holder for releasably securing the suture segment to the base; and,
c. a grasp engagement element holder for releasably securing the grasp engagement element to the base.

Embodiment 38

The package of embodiment 37, wherein the segment holder and grasp engagement element holder are positioned to segregate the segment and the grasp engagement element.

Embodiment 39

The package of embodiment 37, further comprising an additional segment holder.

Embodiment 40

The package of embodiment 39, wherein the additional segment holder is adapted to segregate an additional segment from the segment and the grasp engagement element.

Embodiment 41

The package of embodiment 37, wherein the grasp engagement element holder is adapted for contacting the device at or near the grasp engagement element while securing the grasp engagement element to the base.

Embodiment 42

The package of embodiment 37 or 38, wherein the segment holder is adapted for contacting the device at or near the segment distal end while securing the segment to the base.

Embodiment 43

The package of embodiment 37 or 38, wherein at least one holder comprises multiple sections.

Embodiment 44

The package of embodiment 37 or 38, wherein at least one holder is removable from the package.

Embodiment 45

The package of embodiment 37 or 38, further comprising a segment guide for positioning a portion of the at least one suture segment.

Embodiment 46

The package of embodiment 37, wherein the segment holder is a needle park.

Embodiment 47

The package of embodiment 37, further comprising an outer housing.

Embodiment 48

The package of embodiment 47, wherein the outer housing is adapted to hold at least one of a needle driver and a scissors.

Embodiment 49

A trauma kit comprising:
d. an outer housing;
e. a suture package containing a self-retaining suture having a grasp engagement element attached to at least one suture segment.

Embodiment 50

The kit of embodiment 49, further comprising at least one of a needle driver and scissors.

Embodiment 51

A removable bidirectional self-retaining suture, the suture comprising:
a. a suture body having a first end, a second end, and a periphery;

b. a plurality of retainers, the retainers on a first portion of the suture between the first end of the suture and a first axial location on the suture for permitting movement of the suture through tissue in a direction of movement of the first end and preventing movement of the suture through tissue in a direction opposite the direction of movement of the first end, and the retainers on a second portion of the suture between the second end of the suture and a second axial location on the suture permitting movement of the suture through tissue in a direction of movement of the second end and preventing movement of the suture through tissue in a direction opposite the direction of movement of the second end; and
c. a grasp engagement element between the first and second axial locations, the grasp engagement element having at least two apertures through which the suture body is threaded between the first and second axial locations.

Embodiment 52

The suture of embodiment 51, wherein at least one aperture of the grasp engagement element comprises a sharp edge.

The details of one or more embodiments are set forth in the description below. Other features, objects and advantages will be apparent from the description, the drawings, and the claims. In addition, the disclosures of all patents and patent applications referenced herein are incorporated by reference in their entirety.

DESCRIPTION OF DRAWINGS

Features of the invention, its nature and various advantages will be apparent from the accompanying drawings and the following detailed description of various embodiments.

FIG. 1 is a view of an emergency bidirectional suture in accordance with an embodiment of the present invention, the suture having a closed loop grasp engagement element.

FIG. 2 is a view of an emergency bidirectional suture in accordance with another embodiment of the present invention, the suture having a closed loop grasp engagement element.

FIG. 3 is a view of an emergency bidirectional suture in accordance with another embodiment of the present invention, the suture having a tabbed grasp engagement element.

FIG. 4 is a view of an emergency bidirectional suture in accordance with another embodiment of the present invention, the suture having an open polygonal grasp engagement element.

FIG. 5 is a view of an emergency bidirectional suture in accordance with still another embodiment of the present invention, the suture having an open loop grasp engagement element.

FIG. 6 is a view of an emergency bidirectional suture in accordance with still another embodiment of the present invention, the grasp engagement element including tissue stops.

FIGS. 8a and 8b are perspective views of a use of an embodiment according to the present invention of an emergency bidirectional suture.

FIG. 9 is a perspective view of a use of an embodiment according to the present invention of an emergency bidirectional suture.

FIGS. 14A, 14B and 15 are views of emergency deployment suture in accordance with the invention, where the suture is shown in the context of optional packaging material for the suture, where FIG. 14B is an enlarged view of a portion of the suture shown in FIG. 14A.

DESCRIPTION OF INVENTION

Definitions

Figure 7:
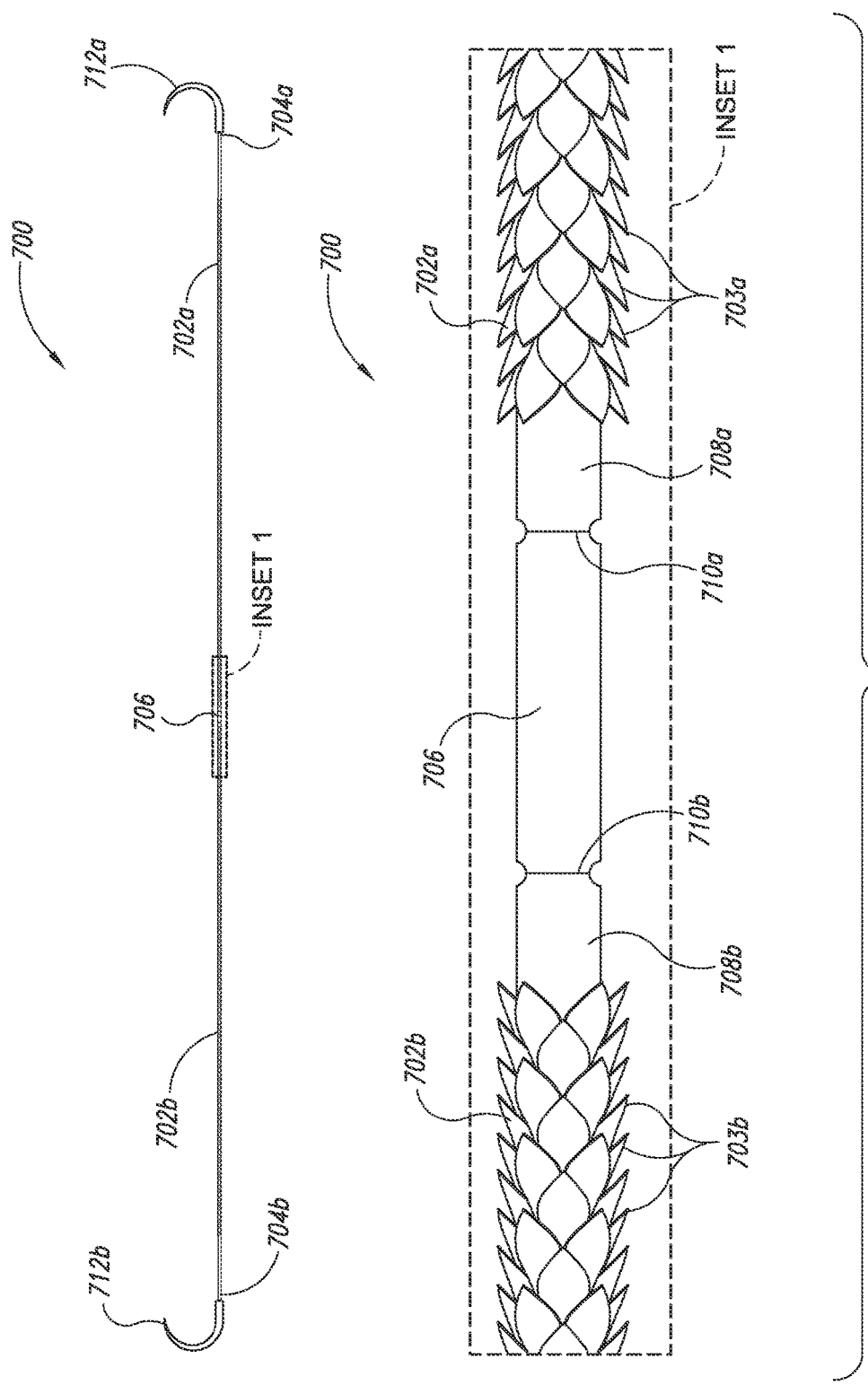
FIG. 7 is a view of an emergency bidirectional suture in accordance with still another embodiment of the present invention, including a detachable grasp engagement element.

Definitions of certain terms that may be used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor.

"Tissue retainer" (or simply "retainer") or "barb" refers to a physical feature of a suture filament which is adapted to mechanically engage tissue and resist movement of the suture in at least one axial directions, and preferably prevent such movement. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the physician, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In one embodiment, the emergency sutures described herein are prepared from one or more segments of filament that each comprise a plurality of cuts, that is, cuts have been made in the filament using a blade or a laser or other suitable cutting instrument, and those cuts create and provide for retainers that can fan out from the filament. Retainers formed in this way are advantageous because when the segment is pulled through tissue, the retainers can retract into the body of the filament and thus contribute little, and preferably no resistance to the movement of the suture segment through the tissue, during the time when the suture segment is being deployed into the wound or other area needing a suture. The cuts made in the filament are preferably not too deep, so as to minimize a reduction in the tensile strength of the filament caused by the presence of the cuts, where cut depths of less than about 5%, or less than about 10%, 15%, 20%, or 25% of the cross-sectional distance of the filament are provided in different optional embodiments of the invention, with 5-25% or 5-20% or 5-15% being ranges present in optional embodiments of the invention. The retainers created by cutting a filament will have a topside composed of the outer surface of the filament, and an underside formed by the cut and composed of the material that forms the inside of the filament. In various optional embodiments of the present invention, a particular cut may create a retainer having an underside that lies within a single plane, that is, the cut may be a single straight cut, or the cut may create a retainer having an underside that lies in two planes, that is, the cut may following a first trajectory for a first distance and then a second trajectory for a second distance. Retainers having undersides lying within two different planes may be advantageous where the first plane cuts into and toward the center of the filament, typically with some concomitant cutting along the longitudinal axis of the filament, effectively establishing a depth of cut, while the subsequent second plane travels along the longitudinal axis of the filament but with little or no movement toward the center of the filament, effectively establishing a retainer length. When filaments having a plurality of cuts are utilized to provide for segments comprising retainers, the underside of the retainer will join to the filament along a baseline, where this baseline may be straight or may be arcuate. An arcuate baseline may be advantageous in assisting the retainer to "fan out". In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth. These are sometimes also referred to as "barb configurations".

"Transition segment" or "transition portion" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" or refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and U.S. Pat. No. 5,464,422 (W. L. Gore, Newark, Del.); and U.S. Pat. Nos. 5,941,899; 5,425,746; 5,306,288 and 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

Emergency Self-Retaining Sutures and Systems

In accordance with particular embodiments, the present invention provides emergency self-retaining sutures and systems which are unidirectional, bidirectional, multidirectional. The sutures and systems of the present invention include a grasp engagement element to facilitate removal of the emergency suture or system; in some embodiments, the grasp engagement element may be adapted to engage fingers, while in other embodiments it may be adapted to engage surgical tools (such as tweezers). It is also configured to be easily detectable, whether due to its size, shape, colour, texture, or any combination thereof. To remove an emergency suture or system of the present invention from a wound closure, the grasp engagement element may, in some embodiments, be grasped (again, by fingers or surgical tools) and severed from the rest of the suture and thus permit each self-retaining segment to be removed from the tissue in the direction it was originally deployed. In other embodiments, the grasp engagement element may be grasped and then each self-retaining segment severed from the grasp engagement element and from each other to facilitate the subsequent removal of the self-retaining segments. Grasp engagement elements may be provided with any number of configurations, including continuous loops (including circular and elliptical loops), polygons, handled loops, tabs, partial loops, and partial polygons. They include tissue stops at each end, to inhibit passage of the grasp engage element into the tissue. They may be rigid or flexible.

According to particular embodiments of the present invention, these emergency sutures and suture systems and/or sections thereof may be unmarked, marked or differentially-marked by one or more types of markers or combination of markers to facilitate the differentiation of the grasp engagement element from the rest of the device.

To serve the purpose of allowing the soldier or medical personnel to identify the grasp engagement element, any visible marking used should be readily recognized and distinguished by the soldier or medical personnel under the conditions in which the suture is to be used. For example, for a battlefield or field hospital, the marking of the grasp engagement element would desirably be readily visible to the naked eye in low light conditions.

The markers can be provided in various forms that may be identified and distinguished from one another. The markers may comprise distinguishable, patterns, shapes, lengths, colors sizes, directions and arrangements. The markers can include different colors such as red, green, orange, yellow, green, blue etc. Such colors may be used in a uniform density or varying density in which case the graduation of color density may be used to designate e.g. an orientation. The markers may be included along the entire length of the self-retaining suture system, at a number of discrete points, or only at the ends or transition section of the self-retaining suture. In some cases it may be desirable to use a color for markers that is uncommon in the operative environment. For example, it may be desirable to use green markers because green is not common in the human body.

The markers can be formed by various conventional methods. For example, the markers can be coated, sprayed, glued, dyed, stained, or otherwise affixed to the self-retaining suture systems or components thereof. Traditional colourant application processes include, without limitation, dipping, spraying (by, for example, an ink jet), painting, printing, applying and/or coating colourants on the suture section of interest. Critical fluid extraction (such as carbon oxide) may also be used to add colourant locally to all or part of the section desired to be marked. Alternatively, colourant(s) for the suture section of interest may be included in a portion of the suture material that is used to form the suture body, wherein that portion is in the section of interest of the manufactured suture.

Additionally, the colourant(s) employed for demarcating the suture section of interest may be included on a plastic biocompatible material which is applied on the suture at the section of interest. Such a layer may be absorbable, such as polyglycolide coating which has a colourant to mark the suture section of interest, or it may be a non-absorbable material, such silicone. The coloured material may be synthetic or may be derived from a natural source (whether the material be modified or unmodified), such as collagen.

Alternatively, the suture section of interest may be reverse-marked, such that where the suture body is already visibly coloured, the colourant may be absent from all or part of the suture section of interest such that at least a portion of the section of interest is optically distinguishable by the surgeon from the rest of the suture. Such a suture may manufactured by including a colourant-free portion of suture material in the suture section of interest area during the manufacture of the suture body (for example, by extrusion) or by removal of colourant from the suture section of interest after the suture body has been manufactured, whether before or after retainers have been formed on the suture body. Colourant may be removed locally by, for example, critical fluid extraction such as (e.g., carbon oxide). It is not necessary to remove all of the colourant from the section of interest of the suture as long as there is a difference detectable by a surgeon between the section of interest and the rest of the suture.

Another example of a reverse-marked suture is one that lacks a coloured layer that is present on the rest of the suture body. A plastic biocompatible material bearing a colourant may be applied on the other sections of the suture, and at least where the other sections border the section of interest. Examples of such materials are discussed above. As in the foregoing examples, demarcating the suture section of interest may be effected in the suture manufacturing process either before or after forming retainers.

Another example of a reverse-marked suture is one having a coaxial structure wherein each coaxial layer having a different colour, and a portion of the outermost layer(s) is removed to visually expose a layer below. For example, a dual-layer monofilament polypropylene suture can be produced with a white inner core (intercoaxial layer) with a blue outer coaxial layer, and portions of the outer layer can be removed to visually expose the white inner monofilament to mark the suture section of interest.

Yet another example of a reverse-marked suture is one in which an external coating is removed (or partially removed) from the suture in the suture section of interest, and where either the coating or base suture has a contrasting colour difference. This technique of removing (or partially removing) material in the suture section of interest may also create a tactile demarcation of the suture section of interest.

As described above, the grasp engagement element or detachment regions may be marked to enable that section to be identified and distinguished from other sections instead of, or in addition to, marking the suture filament itself. If such marking is present in a wavelength range other than the visible wavelength range, a detector would be used to located and image the non-visible marker so that field hospital personnel would have the use and benefit of this marker.

Bidirectional Emergency Sutures

Embodiments of bidirectional emergency sutures in accordance with the present invention are shown in FIGS. 1-7. In FIG. 1, the suture 100 includes a first self-retaining suture segment 102a, a second self-retaining suture segment 102b, and a grasp engagement element 106 comprising a ring 106a. In general, the ring 106a may be any shape that allows someone to put his or her finger through the ring, so as to allow the person to then pull the ring away from the first and second self-retaining suture segments 102a and 102b. For example, the ring may be round, as shown in FIG. 1, or it could be oval or polygonal or other shape, so long as the ring comprises an opening or aperture. The grasp engagement element 106 is joined to proximal end 108b of segment 102b and to proximal end 108a of segment 102a, preferably at different locations along the ring 106a as shown in FIG. 1. First self-retaining suture segment 102a includes a plurality of retainers 103a oriented to, when in tissue, permit movement of the segment 102a through tissue in a direction of movement of distal or deployment end 104a and resist movement of the suture through tissue in a direction opposite the direction of movement of distal end 104a. Conversely, second self-retaining suture segment 102b includes a plurality of retainers 103b oriented to, when in tissue, resist movement of the segment 102b through tissue in a direction of movement of the distal or deployment end 104b of the second segment 102b and resist movement of the segment through tissue in a direction opposite the direction of movement of the end 104b. Optionally, segment 102a may be affixed to a needle 112a, and optionally segment 102b may be affixed to a needle 112b, where either or both needles may optionally be curved as shown in FIG. 1.

FIG. 2 illustrates another embodiment of an emergency suture having looped grasp engagement element. The suture 200 includes a first self-retaining suture segment 202a, a second self-retaining suture segment 202b, and a grasp engagement element 206 (in the form of a ellipse 206a at end of a handle 206b) at the proximal ends 208a and 208b of segments 202a and 202b, respectively. First self-retaining suture segment 202a includes a plurality of retainers 203a oriented to, when in tissue, permit movement of the segment 202a through tissue in a direction of movement of distal end 204a of segment 202a, and resist movement of the suture through tissue in a direction opposite the direction of movement of the distal end 204a. Conversely, second self-retaining suture segment 202b includes a plurality of retainers 203b oriented to, when in tissue, permit movement of the segment 202b through tissue in a direction of movement of the distal end 204b of the second segment 202b and resist movement of the segment 202b through tissue in a direction opposite the direction of movement of the distal end 204b. Optionally, segment 202a may be affixed to a needle 212a, and optionally segment 202b may be affixed to a needle 212b, where either or both needles may optionally be curved as shown in FIG. 2.

An embodiment of an emergency suture in accordance with the present invention illustrated in FIG. 3 and includes a grasp engagement element 306 in the form of a tab, located between end 308a of a first self-retaining suture segment 302a and end 308b of a second self-retaining suture segment 302b. The grasp engagement element 306 is provided with a variably textured surface 310 to enhance the ability of someone to grip of the grasp engagement element 306, where the texturing may take the form of raised ridges or other uneven surface as illustrated in FIG. 3. First self-retaining suture segment 302a includes a plurality of retainers 303a oriented to, when in tissue, permit movement of the segment 302a through tissue in a direction of movement of distal end 304a of the segment 302a, and resist movement of the segment 302a through tissue in a direction opposite the direction of movement of the distal end 304a. Conversely, second self-retaining suture segment 302b includes a plurality of retainers 303b oriented to, when in tissue, permit movement of the segment 302b through tissue in a direction of movement of the distal end 304b of the second segment 302b and resist movement of the segment through tissue in a direction opposite the direction of movement of the distal end 304b. Optionally, segment 302a may be affixed to a needle 312a, and optionally segment 302b may be affixed to a needle 312b, where either or both needles may optionally be curved as shown in FIG. 3.

Providing texture differences to all or part of the grasp engagement element 306 includes providing a plurality of areas of increased and/or decreased suture body diameter along the grasp engagement element 306. For example, a plurality of indentations, a plurality of relief configurations, and any combinations thereof may be provided in the section of interest, by methods including, without limitation, compression, cutting, coating, application of agents such as abrasives, polymerisers, acid etchants, base etchants, and so forth.

FIGS. 4 and 5 illustrate embodiments having grasp engagement elements 406 and 506, respectively, in two variations on an open loop form. In FIG. 4, the grasp engagement element 406 is an open polygon and is located between proximal end 408a of a first self-retaining suture segment 402a and proximal end 408b of a second self-retaining suture segment 402b. First self-retaining suture segment 402a includes a plurality of retainers 403a oriented to, when in tissue, permit movement of the segment 402a through tissue in a direction of movement of distal end 404a and resist movement of the segment 402a through tissue in a direction opposite the direction of movement of the distal end 404a. Conversely, second self-retaining suture segment 402b includes a plurality of retainers 403b oriented to, when in tissue, permit movement of the segment 402b through tissue in a direction of movement of the distal end 404b of the second segment 402b and resist movement of the segment through tissue in a direction opposite the direction of movement of the distal end 404b. Optionally, segment 402a may be affixed to a needle 412a, and optionally segment 402b may be affixed to a needle 412b, where either or both needles may optionally be curved as shown in FIG. 4.

In FIG. 5, the grasp engagement element 506 is shown as an open loop and is located between proximal end 508a of a first self-retaining suture segment 502a and proximal end 508b of a second self-retaining suture segment 502b. First self-retaining suture segment 502a includes a plurality of retainers 503a oriented to, when in tissue, permit movement of the segment 502a through tissue in a direction of movement of distal end 504a and resist movement of the segment through tissue in a direction opposite the direction of movement of the distal end 504a. Conversely, second self-retaining suture segment 502b includes a plurality of retainers 503b oriented to, when in tissue, permit movement of the segment 502b through tissue in a direction of movement of the distal end 504b of the second segment 502b and resist movement of the segment 502b through tissue in a direction opposite the direction of movement of the distal end 504b. In some embodiments having an open loop or open polygon grasp engagement element, the element may be made of rigid or semi-rigid materials, or may be coated to effectuate rigidity or partial rigidity. Optionally, segment 502a may be affixed to a needle 512a, and optionally segment 502b may be affixed to a needle 512b, where either or both needles may optionally be curved as shown in FIG. 5.

FIG. 6 illustrates another embodiment of an emergency suture having an open looped grasp engagement element. The suture 600 includes a first self-retaining suture segment 602a, a second self-retaining suture segment 602b, and a grasp engagement element 606. Grasp engagement element 606 is provided with tissue stops 610a and 610b, adjacent to the proximal ends 608a and 608b of first and second self-retaining suture segments 602a and 602b, respectively. The tissue stops 610a and 610b each have a cross-sectional distance that is greater than the cross-sectional distance of the of the adjacent proximal ends 608a and 608b, respectively, and thus are configured to prevent slippage of the grasp engagement element 606 into tissue when the suture 600 is located within tissue and functioning in a wound closure. First self-retaining suture segment 602a includes a plurality of retainers 603a oriented to, when in tissue, permit movement of the segment 602a through tissue in a direction of movement of distal end 604a and resist movement of the segment through tissue in a direction opposite the direction of movement of the distal end 604a. Conversely, second self-retaining suture segment 602b includes a plurality of retainers oriented to, when in tissue, permit movement of the segment 602b through tissue in a direction of movement of the distal end 604b of the second segment 602b and resist movement of the segment 602b through tissue in a direction opposite the direction of movement of the distal end 604b. Optionally, segment 602a may be affixed to a needle 612a, and optionally segment 602b may be affixed to a needle 612b, where either or both needles may optionally be curved as shown in FIG. 6.

In yet another embodiment, as illustrated in FIG. 7, the grasp engagement element is 706 of suture 700 is bounded by detachment elements 710a and 710b, which are adjacent to the proximal ends 708a and 708b of first and second self-retaining suture segments 702a and 702b, respectively. Detachment elements 708a and 708b are adapted to require only a sharp tug to cause the removal of the element 706 from suture 700, and may comprise frangible material, a smaller diameter of suture material (thereby having less tensile strength than adjacent portions of the suture), or detachable connectors. First self-retaining suture segment 702a includes a plurality retainers 703a oriented to, when in tissue, permit movement of the segment 702a through tissue in a direction of movement of distal end 704a and resist movement of the segment through tissue in a direction opposite the direction of movement of the distal end 704a. Conversely, second self-retaining suture segment 702b includes a plurality of retainers 703b oriented to, when in tissue, permit movement of the segment 702b through tissue in a direction of movement of the distal end 704b of the second segment 702b and resist movement of the segment through tissue in a direction opposite the direction of movement of the distal end 704b. Optionally, segment 702a may be affixed to a needle 712a, and optionally segment 702b may be affixed to a needle 712b, where either or both needles may optionally be curved as shown in FIG. 7.

Figure 15:
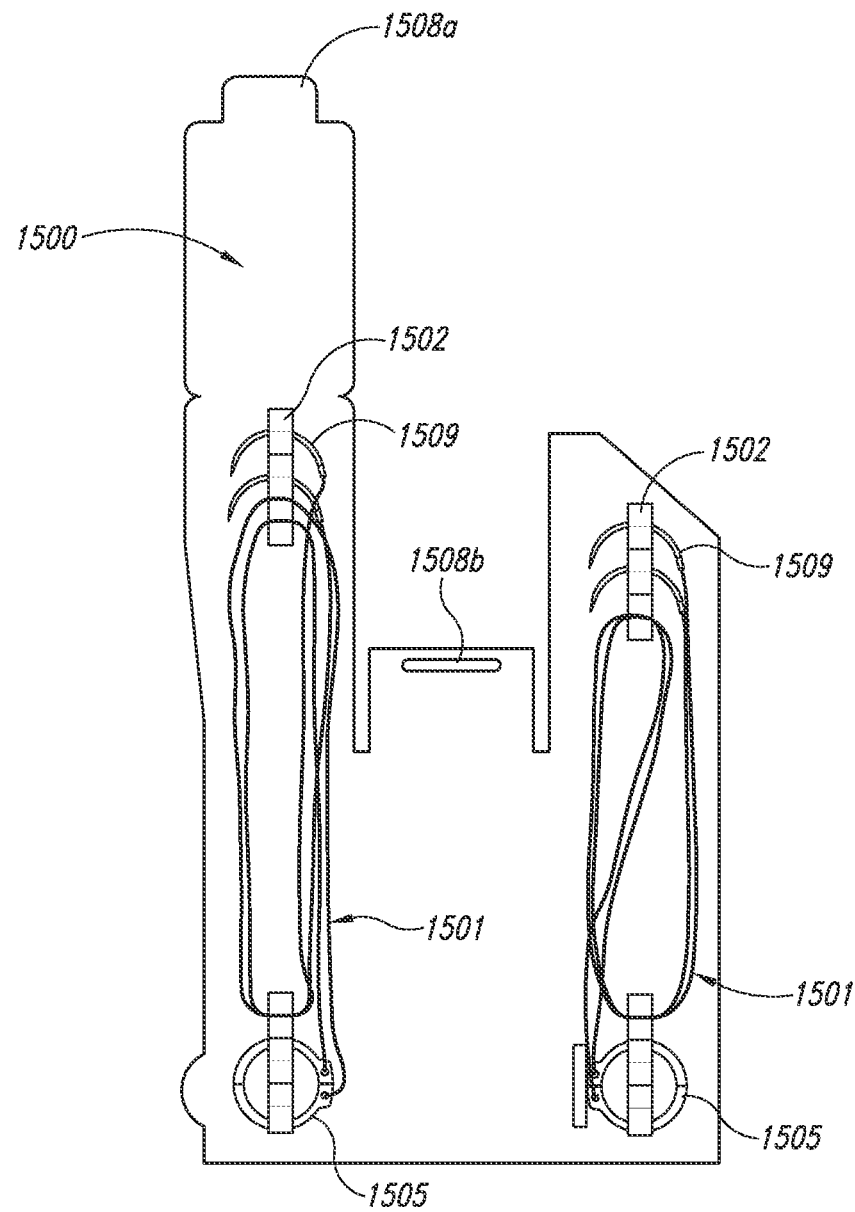

FIGS. 14A, 14B and 15 include depictions of yet another embodiment of an emergency deployment suture in accordance with the invention, where the suture is shown in the context of optional packaging material for the suture. Bidirectional suture 1401 in FIG. 14A includes first and second self-retaining suture segments 1403a and 1403b, respectively, with needles 1409a and 1409b at their respective distal ends 1411a and 1411b. In one embodiment, grasp engagement element 1405 attaches to the proximal ends 1413a and 1413b of the first and second self-retaining suture segments 1403a and 1403b, respectively, by way of being tied or otherwise joined to apertures 1407a and 1407b of the grasp engagement element 1405. In an alternative embodiment, illustrated in FIG. 14B, proximal ends 1413a and 1413b each attach to an end of a transition segment shown as dashed line 1415, where transition segment 1415 may be retainer-free filament or some other filament, thereby linking together the proximal ends 1413a and 1413b, where in this embodiment the suture 1401 passes through the apertures 1407a and 1407b at or near the transition segment. FIG. 14B shows regions 1417a and 1417b, which are optionally present as part of grasp engagement element 1405, where regions 1417a and 1417b are frangible regions of the grasp element 1405 and are thus adapted to be readily snapped or broken apart. To remove a suture such as 1401 having a grasp engagement element 1405 with two frangible regions 1417a and 1417b, from a wound closure, the grasp engagement element 1405 could be broken and the resulting pieces held apart to expose the suture, e.g., the transition segment 1415, for easy cutting. Similarly, in FIG. 15, bidirectional suture 1401 as described in relation to FIG. 14A is renumbered 1501 and includes grasp engagement element 1505 having apertures 1507a and 1507b engaging the suture 1501 at or near a transition segment of the suture 1501. Optionally, grasp engagement element 1505 may contain one, preferably two, or more than two frangible regions, and thus may be adapted to be snapped or broken apart. In some embodiments, one or more suture apertures of a grasp engagement element, such as those illustrated in FIGS. 14 and 15, may include a sharpened edge that would allow one to remove the grasp engagement while severing the suture, thus enabling easy removal of the suture from a wound closure.

Figure 8A:
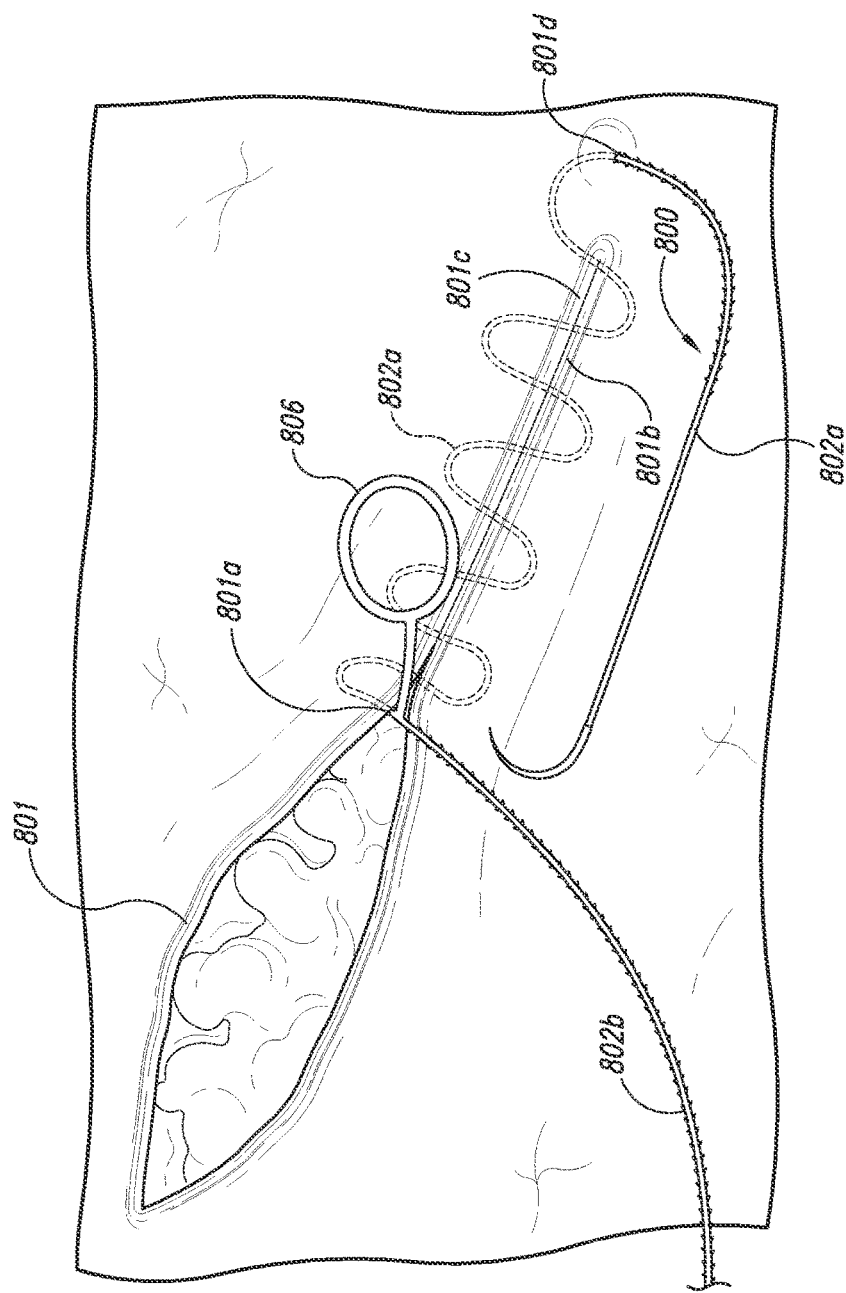

Grasp engagement element 806 is depicted in FIGS. 8a and 8b. With reference to FIG. 8a, grasp engagement element 806 is engaged to each of first and second self-retaining suture segments 802a and 802b, respectively, and is positioned outside the wound 801. A first self-retaining suture segment 802a of suture 800 is deployed in a subcuticular stitch through wound edges 801b, starting at about the central portion 801a of the wound 801 and moving toward one end 801c of the wound 801, and then suture 800 is pulled in the deployment direction (that is, the direction of the end of the wound 801c) to approximate the wound edges 801a together. Dashed line 802a illustrates the first self-retaining suture segment 802a positioned underneath the tissue. Then, as illustrated in FIG. 8b, the process is repeated for the rest of the wound with the second self-retaining suture segment 802b (shown as a dashed line, representing its location within the tissue), resulting in a closed wound. When, on the second half of the wound closure, suture 800 is drawn through the tissue to approximate the wound edges on the open remainder of the wound, the act of pulling the suture 800 in the second deployment direction (that is, towards the second end of the wound 801e) comprises the necessary affixation force for the plurality of retainers on segment 802a, thus causing tissue engagement. Conversely, once suture 800 is pulled sufficiently tightly to close the second half of the wound, the engagement force of the tissue exerted against the plurality of retainers on the first segment 802a affixes the plurality of retainers on second segment 802b. To remove the suture from the tissue, the grasp engagement element 806 is grasped and the suture segments 802a and 802b are severed from each other and from the element 806. Then suture segment 802a is pulled out of the tissue from the suture exit point 801*d* and suture segment 802*b* is similarly pulled out of the tissue from the respective suture exit point 801*f*.

Another use of an emergency bidirectional suture is illustrated in FIG. 9, to bring wounds under high tension closer together to hold them in place until a definitive surface closure can be performed. In a gaping wound (or a wound that would be difficult to bring together because of tension across it), a bidirectional emergency suture 900 is deployed to bring the tissues into closer approximation. In this procedure, the grasp engagement element 906 is positioned at about the midpoint of the wound and self-retaining segment 902 is inserted through the wound edge, passed radially outwards from wound, and withdrawn at a distance from the wound edge at exit point 908; the distance is selected to suit the nature of the wound and surrounding tissues, while bearing in mind that the farther the distance, the greater the holding strength. The procedure is then repeated on the other side of the wound with self-retaining segment 904. For large wounds, several sutures may be required. The tissue can then be progressively "ratcheted" together over the retainers until it is as close together as is required (or as is prudent). Having a grasp engagement element between self-retaining segments 902 and 904 not only facilitates later removal of the suture, but also increases the anchorage of the self-retaining segments on either side of the wound, thereby increasing the amount of tension the suture can withstand without pulling through the tissue.

Unidirectional Emergency Sutures

Figure 10:
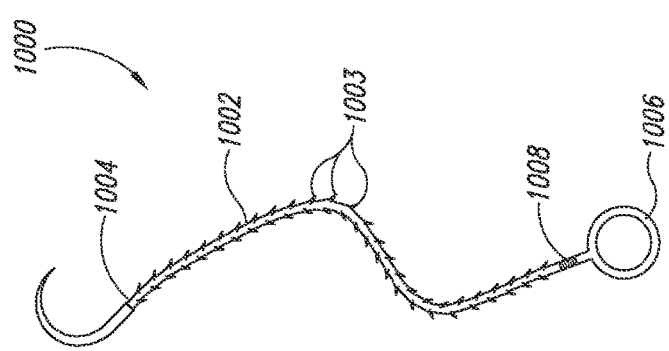
FIG. 10 is a view of an emergency unidirectional suture in accordance with an embodiment of the present invention.

The sutures of the invention also include unidirectional embodiments, as in the example shown in FIG. 10. The suture 1000 includes a self-retaining suture segment 1002 and an anchor element 1006 adjacent to a detachment element 1008 at a proximal end of segment 1002. Self-retaining suture segment 1002 includes a plurality of retainers 1003 oriented to, when in tissue, permit movement of the segment 1002 through tissue in a direction of movement of sharpened end 1004 and resist movement of the suture through tissue in a direction opposite the direction of movement of the end 1004. Once the suture is fully deployed into tissue, the grasp engagement anchor 1006 acts to resist movement of the suture in a direction towards the end 1004. Detachment element 1008 is adapted to require a breaking motion such as sharp tug, bending, or twisting to cause the removal of the element 1006 from segment 1002, and may comprise frangible material, a smaller diameter of suture material (thereby having less tensile strength than other portions of the suture), or detachable connectors.

Multidirectional Emergency Suture Systems

Figure 11:
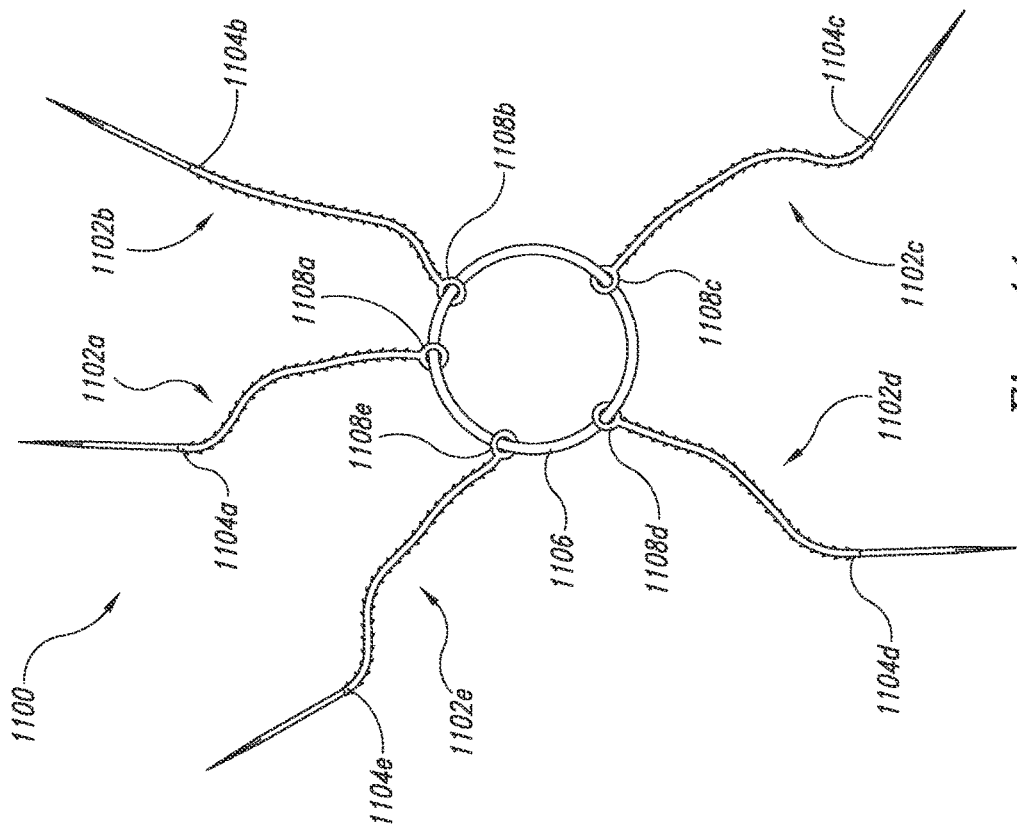
FIG. 11 is a view of an emergency multidirectional suture in accordance with an embodiment of the present invention.

Self-retaining suture systems may comprise more than two suture segments. A self-retaining suture system may have one, two or more suture segments including up to about ten suture segments or more, depending upon the application. For example, as shown in FIG. 11 a suture system 1100 has five self-retaining suture segments 1102*a-e* radiating from a central ring 1106. Each suture segment 1102*a-e* has a needle at its deployment end 1104*a-e*, and a connector 1108*a-e* at its other end, each connector joining its respective suture segment to the ring 1106. The connectors may be manufactured in whole or in part of a frangible material, to facilitate the removal of the ring and subsequent removal of the suture segments from a temporary wound closure once better medical care becomes available to the patient. Alternatively, the connectors may be severed from the suture segments prior to the removal of the suture system.

Figure 12:
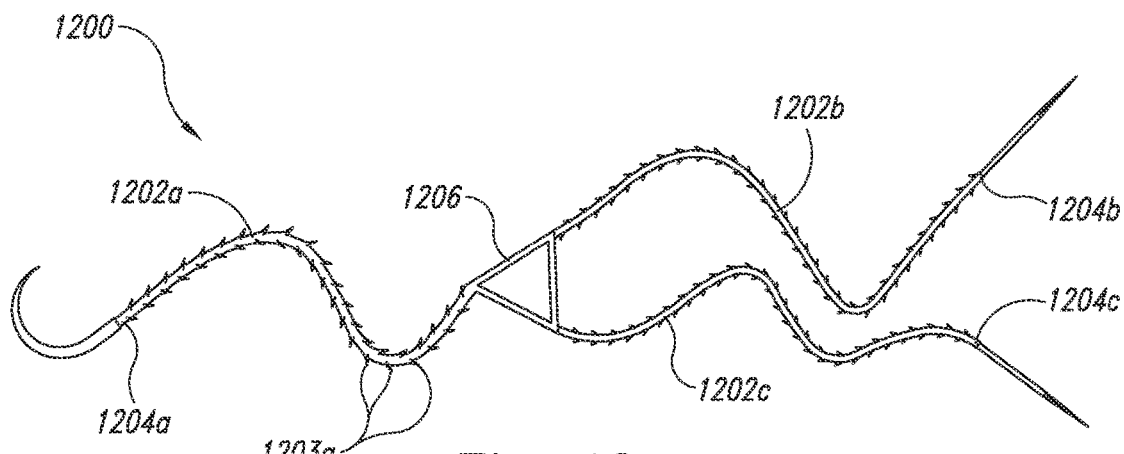
FIG. 12 is a view of an emergency multidirectional suture in accordance with an embodiment of the present invention.

Another embodiment of a multidirectional emergency suture system is illustrated in FIG. 12. Suture system 1200 has three self-retaining suture segments 1202*a-c*. Each of the segments 1202*a-c* is joined at one end, i.e., the proximal end, to a grasp engagement element 1206, which may be of any suitable shape, e.g., circular, oval, or as shown in FIG. 12, polygonal. Each of the segments 1202*a-c* also has a needle 1204*a-c* at the other end, i.e., the distal end. Grasp engagement element 1206 is not a separate component in system 1200 but is instead joined to self-retaining segments 1202*a-c*. They may be joined by melting, gluing, welding or the like or may be formed in one piece. As shown in FIG. 12, self-retaining suture segment 1202*a* has a larger diameter than segments 1202*b* and 1202*c* (and accordingly has a larger and differently configured needle attached thereto). FIG. 12 illustrates one option in a wide range of variations that are possible in multi-arm self-retaining suture systems such as 1200. The arms of the suture system may be individually selected based upon the tissue in which they will be deployed. Note that the retainers 1203*a* on a suture segment such as 1202*a* are configured such that the retainers permit the segment to be deployed in the direction of the needle attached to that arm, i.e., in the distal direction, and resist movement of the suture segment in the direction towards the grasp engagement element, i.e., in the proximal direction, which acts as an anchor as well as facilitating the later removal of the suture system from a temporary wound closure. Thus, the suture segments may be deployed through tissue and the tissue approximated towards element 1206, and the retainers will then hold the tissue in the approximated position and resist movement of the tissue away from element 1206. Note that in some multi-arm systems it may be desirable to have some arms without retainers.

Figure 13:
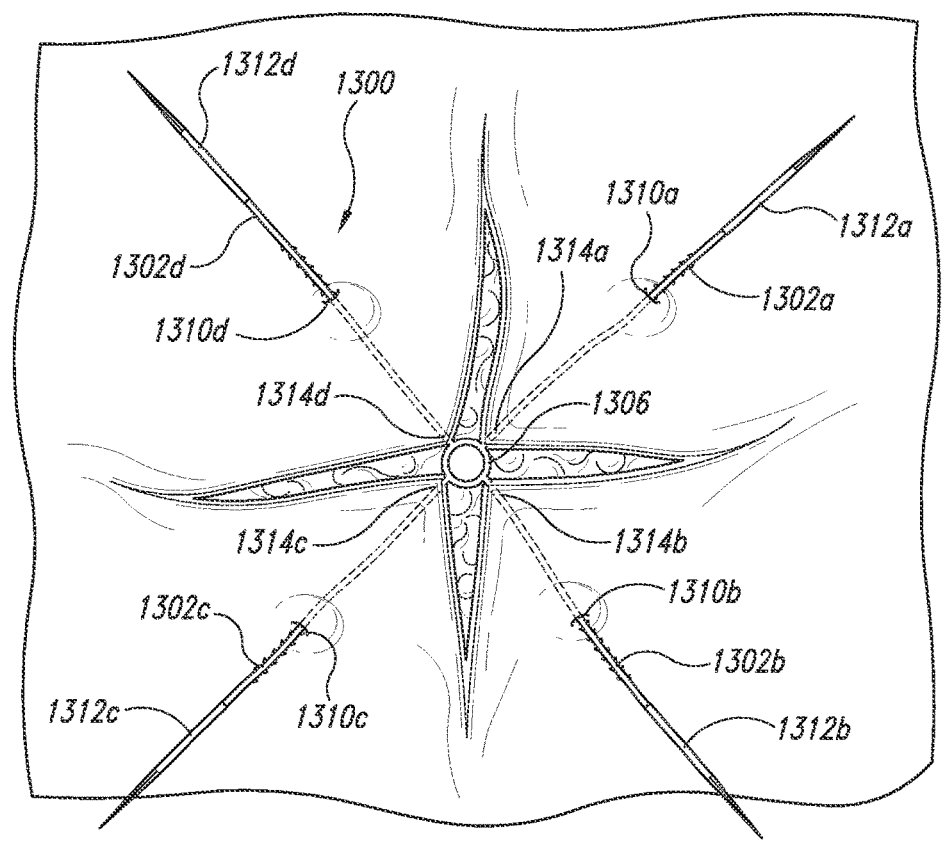
FIG. 13 is a view of a use of an embodiment according to the present invention of an emergency multidirectional suture.

Self-retaining systems having more than two suture segments are useful in applications where it is desirable to have a plurality of suture lines radiating from a common point. Such self-retaining suture systems are useful for example in closes, puncture wounds, stellate wounds and other nonlinear wounds. Such wounds can be produced by blunt trauma, gunshots, explosions and the like and are quite difficult to close with regular suturing techniques. FIG. 13 illustrates a closure of a stellate wound with a multidirectional emergency suture system 1300. Stellate wounds are nonlinear wounds where several tears through tissue meet at a common point and are difficult to close with regular suturing techniques. However, such a wound can be readily closed using a multi-directional system having a self-retaining suture segment for each tissue apex. As shown in FIG. 13, system 1300 comprises four self-retaining suture segments 1302*a-d* each having a needle 1312*a-d* at one end, i.e., the proximal end, and joined at a grasp engagement element 1306 at the other end, i.e., the distal end. Each needle 1312 is inserted at the apex 1314*a-d* of a tissue flap and drawn through the tissue to an exit point 1310*a-d* located a distance away from the wound. After closing the central wound, the remaining linear wounds may be closed further if necessary using standard techniques, such as with conventional or self-retaining sutures (unidirectional or bidirectional).

Packaging of Emergency Self-Retaining Sutures

Sutures and systems described herein may be loaded into packaging adapted to prevent tangling of the suture segments, ends, and grasp engagement elements, and to provide easy removal of the suture or system from the package.

An embodiment of a package is shown in FIG. 14A, where the package is shown holding two different emergency self-retaining suture system. The package includes a base 1400, grasp engagement element holders 1404 and suture segment holders 1402 positioned some distance away from each other on base 1400. Holders may be provided with multiple sections; for example, suture segment holder 1402 provides multiple passages 1402a and 1402b so that each needle on a suture may be segregated from the other. Similarly, grasp engagement element holder 1404 may be provided with multiple sections by placing multiple passages 1404a and 1404b so that suture segments 1403 may be segregated from one another (to prevent tangling of the barbs), as is shown on grasp engagement holder 1404. Base 1400 is configured to be folded along lines A and B, and closed at tab/slot combination 1406b. The base may also be folded along line C to protect the end of a longer suture, and closed at tab/slot combination 1408b.

In another embodiment shown in FIG. 15, the packaging includes a base 1500, grasp engagement element holders 1504 and suture segment holders 1502 positioned some distance away from each other on base 1500. Both grasp engagement holders 1504 and suture segment holders 1502 are provided with multiple sections, allowing suture segments of each suture 1501 to be wound (either in an oval or an alternating arrangement) through the holders and thereby reducing the overall size of the suture/package combination. Base 1500 is configured to be folded and closed at tab/slot combinations 1505a,b. The base may also be folded to protect the end of a longer suture, and closed at tab/slot combination 1506a,b.

Figure 16:
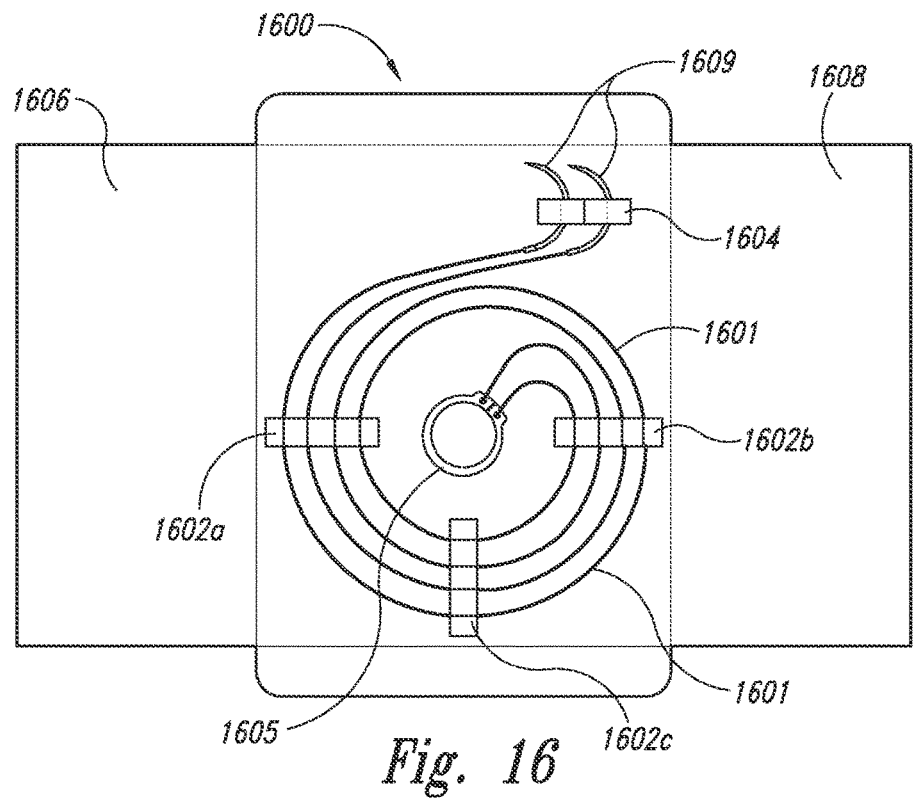
FIG. 16 is a view of packaging of the invention that may be used to store and transport emergency deployment suture.

The embodiment in FIG. 16 includes a base 1600 having three multi-section holders 1602a-c arranged such that two of the holders (1602 a and b) are roughly perpendicularly to a central holder (1602c), where this arrangement of holders permits suture 1601 to be wound in a spiral, with grasp engagement element 1605 at the center of the spiral. Needles 1609 at the ends of the suture are secured to the base at holder 1604, positioned some distance away from holders 1602a-c. Base 1600 further includes one or more of flaps 1606, 1608, 1610 and 1612 which may be folded over to further protect suture 1601. An alternative arrangement having only two multi-section holders 1602 is also an embodiment of the invention.

Figure 17:
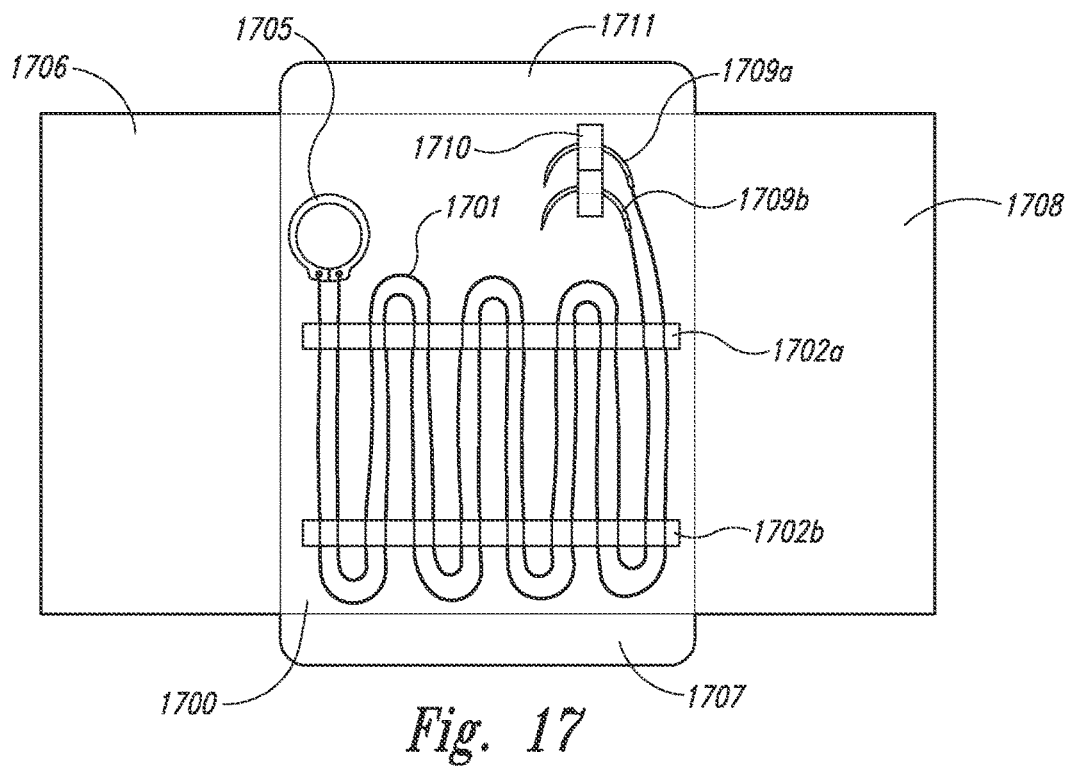
FIG. 17 is a view of packaging of the invention that may be used to store and transport emergency deployment suture.

FIG. 17 illustrates an embodiment in which a suture 1701 may be secured in a back-and-forth arrangement, with the use of two extended multi-section holders 1702a and 1702b. Needles 1709a and 1709b are secured at some distance from grasp engagement element 1705 by use of multi-section holder 1710, and one or more of optionally present flaps 1706, 1707, 1708 and 1711 may be folded over the suture to provide additional protection.

Figure 18:
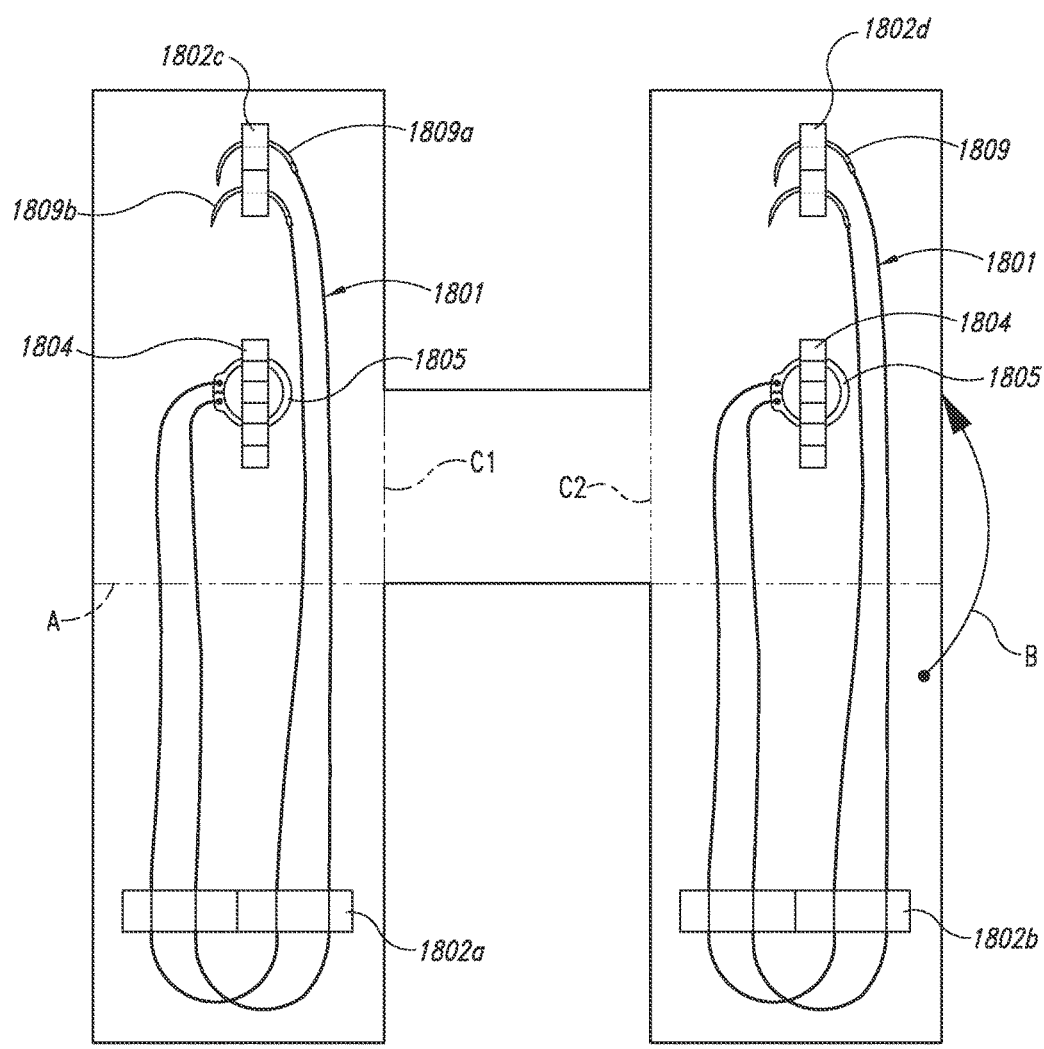
FIG. 18 is a view of packaging of the invention that may be used to store and transport emergency deployment suture.

FIG. 18 illustrates an embodiment in which sutures 1801 may be secured in a "C"-shaped arrangement with multi-section holders 1802a-d. Needles 1809a and 1809b are secured with a multi-section holder near grasp engagement element 1805, which itself is held in place with a multi-section holder 1804, but are disposed sufficiently far away to prevent entanglement. Base 1800 may be folded along line "A" in the direction shown by "B", and optionally along either or both of lines C1 and C2, to reduce the size of the overall package.

Figure 19:
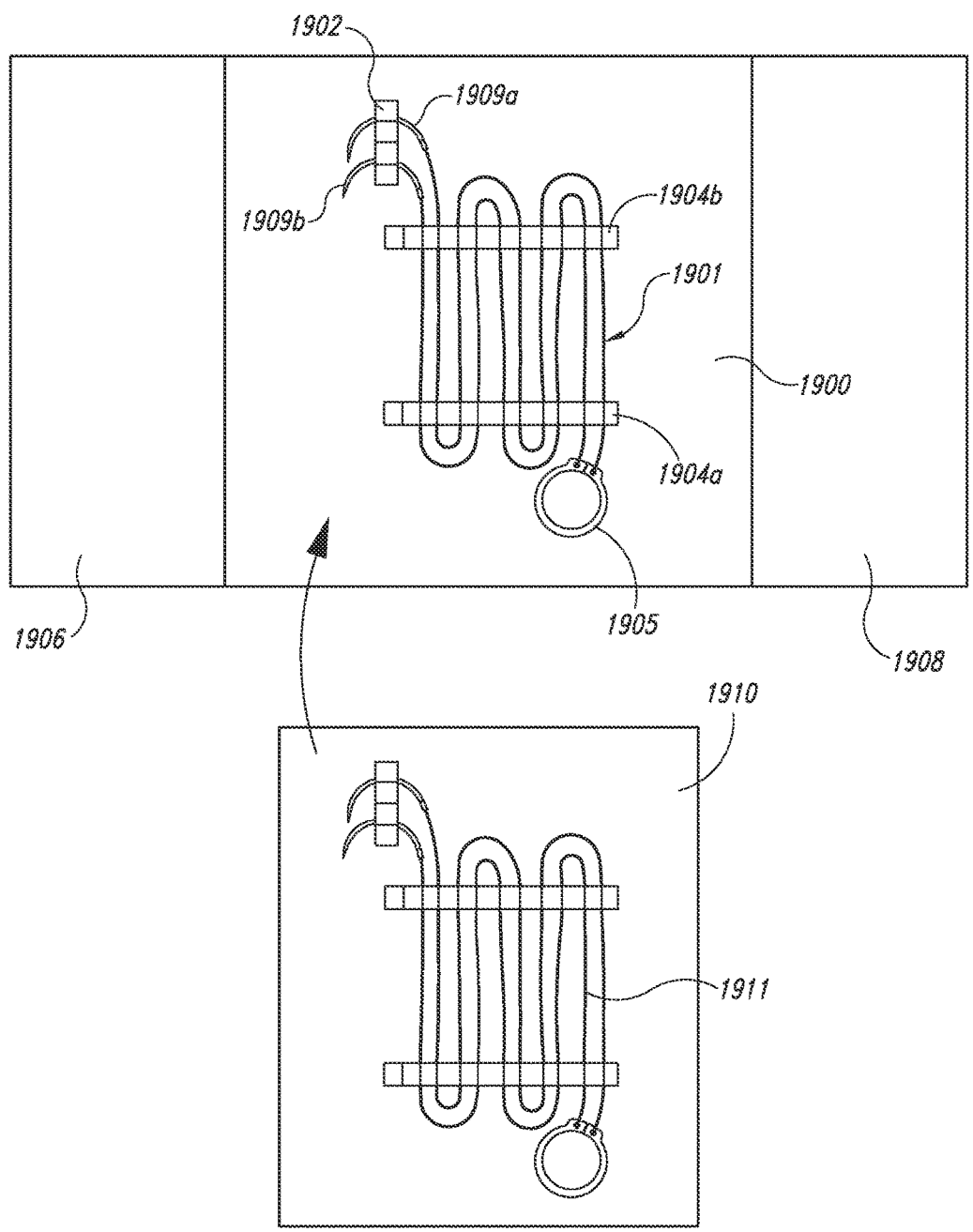
FIG. 19 is a view of packaging of the invention that may be used to store and transport emergency deployment suture.

FIG. 19 illustrates an embodiment in which a suture 1901 may be secured in a back-and-forth arrangement, along extended multi-section holders 1904a and 1904b. Needles 1909a and 1909b are secured with multi-section holder 1902 at some distance from grasp engagement element 1905. Additionally, insert 1910 securing suture 1911 in a similar fashion may be laid over base 1900, and flaps 1906 and 1908 may be folded over the insert to complete cover it.

Figure 20:
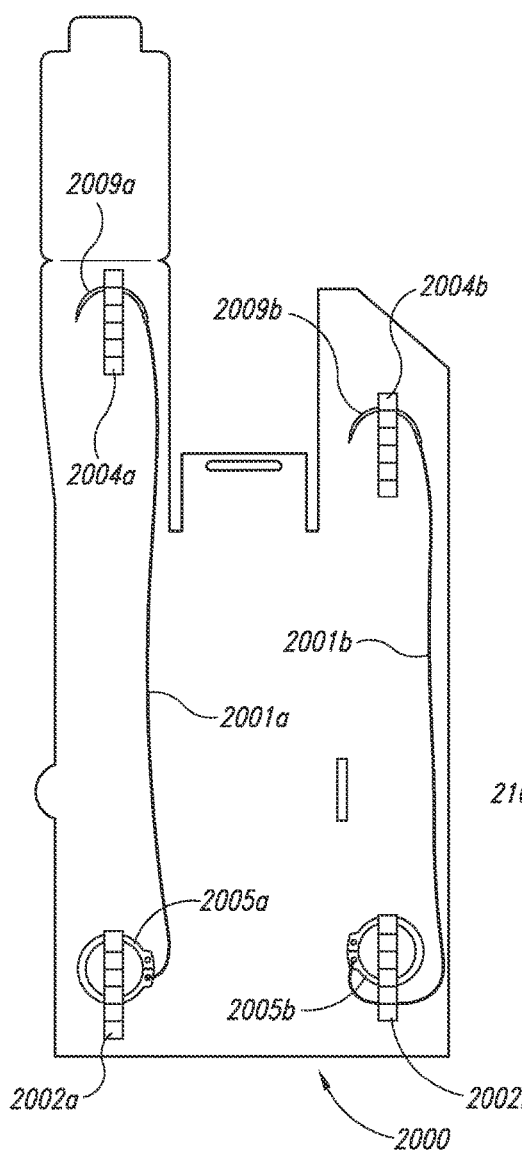
FIG. 20 is a view of packaging of the invention that may be used to store and transport emergency deployment suture.
Figure 21:
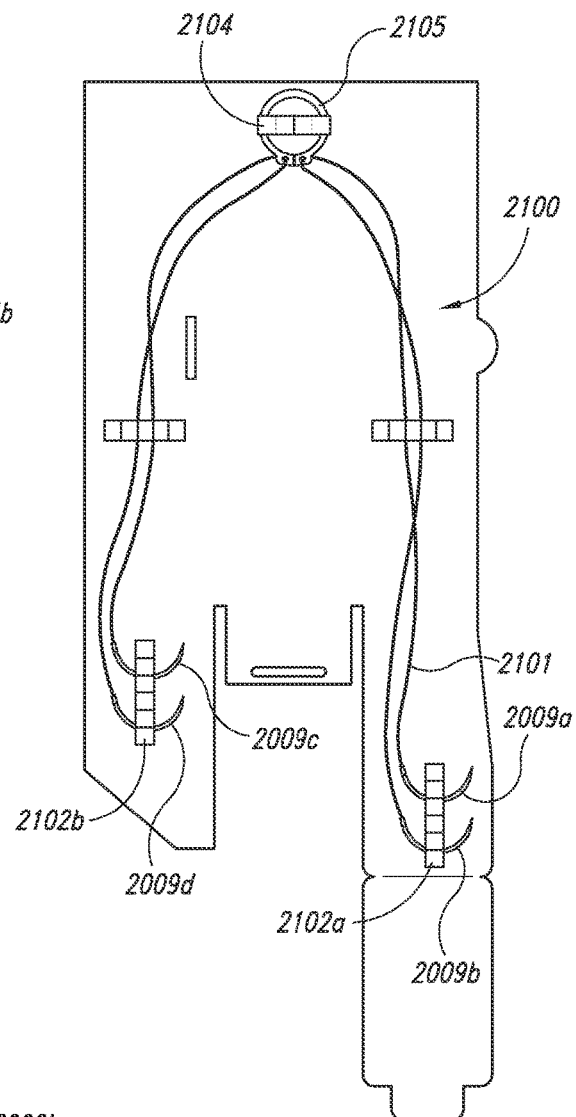
FIG. 21 is a view of packaging of the invention that may be used to store and transport an emergency deployment suture.

FIG. 20 illustrates an embodiment for packaging unidirectional sutures, wherein packaging base 2000 hold unidirectional sutures 2001a and 2001b, the packaging including holders 2002a and 2002b for the grasp engagement elements 2005a and 2005b, respectively, as well as multi section holders 2004a and 2004b for needles 2009a and 2009b, respectively. FIG. 21 illustrates a multi-directional suture packaging on base 2100, in which the various segments of the suture device 2101 are segregated from each other in separate pairs; thus there is only one grasp engagement holder 2105 held securely in place with multi section holder 2104, and multiple suture segment holders 2012a and 2102b which hold needs 2009a, 2009b, 2009c and 2009d.

Figure 22:
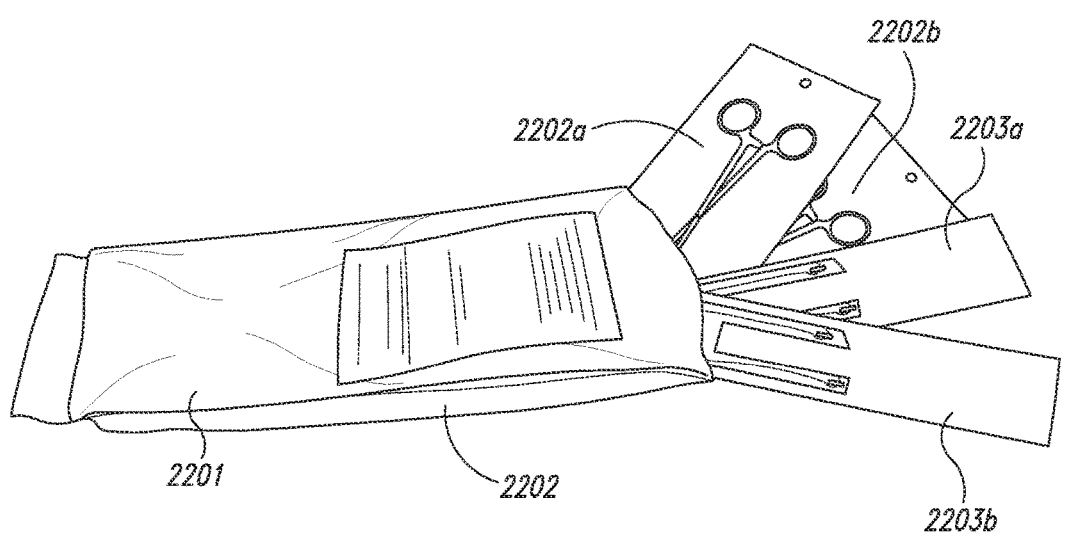
FIG. 22 is a view of packaging of the invention that may be used to store and transport emergency deployment suture and ancillary materials.

FIG. 22 illustrates packaging 2200 which comprises an outer sleeve 2201 in which packaged emergency sutures may be placed, along with related devices such as scissors 2202a and 2202b (although a single pair of scissors may be included), and/or needle drivers 2203a and 2203b (although a single needle driver could be included).

Materials

Suture threads described herein may be produced by any suitable method, including without limitation, injection molding, stamping, cutting, laser, extrusion, and so forth. With respect to cutting, polymeric thread or filaments may be manufactured or purchased for the suture body, and the retainers can be subsequently cut onto the suture body; the retainers may be hand-cut, laser-cut, or mechanically machine-cut using blades, cutting wheels, grinding wheels, and so forth. During cutting either the cutting device or the suture thread may be moved relative to the other, or both may be moved, to control the size, shape and depth of cut 210. Particular methods for cutting barbs on a filament are described in U.S. patent application Ser. No. 09/943,733 titled "Method Of Forming Barbs On A Suture And Apparatus For Performing Same" to Genova et al., and U.S. patent application Ser. No. 10/065,280 titled "Barbed Sutures" to Leung et al. both of which are incorporated herein by reference. The sutures may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

Grasp engagement elements described herein may be produced by any suitable method, including without limitation, injection molding, stamping, cutting, laser, extrusion, and so forth. They may be integrally formed with the suture threads, or the threads and grasp engagement elements may be assembled after manufacture of each component. They may be manufactured from cloth, felt, mesh, plastic (both absorbable and non-absorbable), metallic, or other materials, and may be glued, knotted, crimped or otherwise attached to suture threads. In some embodiments, they may be manufactured from stainless steel or other radio-opaque materials. In some embodiments, they may configured to comfortably accommodate a typical adult finger; suitable diameter ranges may be 0.75" to 1.5", and between 1" to 1.25".

Packaging described herein may be made from any suitable material, such as a combination of paper and synthetic materials, or synthetic materials only, or paper only. Needle holders may be made of foam or other materials that may securely engage needles. The outer sleeves may be manufactured from any suitable materials, including materials permutable to sterilizing gas (such as ethylene dioxide) while preventing microorganism contamination, materials that are compatible with sterilisatoin by gamma radiation, materials that are moisture-resistant (such as foil), and any combinations thereof.

Additionally, sutures and systems described herein may be provided with compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) by inserting the suture into a sleeve or mesh which is comprised of, or coated with, a formulation, or (e) constructing the suture itself with a composition. While compositions including analgesic agents, anti-infective agents, anti-scarring agents, lubricious agents, and anti-inflammatory agents may be generally useful in the emergency situations discussed herein, other such compositions may include without limitation anti-proliferative agents, anti-angiogenic agents, fibrosis-inducing agents, echogenic agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). Coatings may also include a plurality of compositions either together or on different portions of the suture, where the multiple compositions can be selected either for different purposes (such as combinations of analgesics, anti-infective and anti-scarring agents) or for their synergistic effects.

Although the present invention has been shown and described in detail with regard to only a few exemplary embodiments of the invention, it should be understood by those skilled in the art that it is not intended to limit the invention to the specific embodiments disclosed. Various combinations of features, and various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A removable bidirectional self-retaining suture, the suture comprising:
   a. a first end, a second end, and a periphery;
   b. a plurality of retainers, the plurality of retainers located on a first portion of the suture between the first end of the suture and a first axial location on the suture for permitting movement of the suture through tissue in a direction of movement of the first end and preventing movement of the suture through tissue in a direction opposite the direction of movement of the first end, and the plurality of retainers on a second portion of the suture between the second end of the suture and a second axial location on the suture permitting movement of the suture through tissue in a direction of movement of the second end and preventing movement of the suture through tissue in a direction opposite the direction of movement of the second end; and
   c. a grasp engagement element comprising a rigid continuous loop or polygon integrally formed with the suture between the first and second axial locations.

2. The suture of claim 1, wherein the rigid continuous loop comprises a closed ring.

3. The suture of claim 1, wherein the grasp engagement element has a periphery greater than the periphery of the suture.

4. The suture of claim 1, wherein the suture further comprises a frangible portion between the grasp engagement element and the first and second axial locations for facilitating removal of the grasp engagement element from the suture.

5. The suture of claim 1, further comprising a detachable connector connecting the grasp engagement element and the suture.

6. The suture of claim 1, wherein the grasp engagement element comprises a different material than the rest of the suture.

7. A removable multidirectional self-retaining system comprising:
   a. a grasp engagement element comprising a rigid continuous loop or polygon;
   b. at least three suture segments, each suture segment having a plurality of retainers between a first end of the suture segment and a second end of the suture segment for permitting movement of the suture through tissue in a direction of movement of the first end and preventing movement of the suture segment through tissue in a direction opposite the direction of movement of the first end, and a second end of each suture segment being attached to the grasp engagement element such that the grasp engagement element is integrally formed with the plurality of suture segments at the second end.

8. The system of claim 7, wherein the rigid continuous loop comprises a closed ring.

9. A method of emergency wound closure, comprising:
   a. providing a self-retaining suture, the suture having suture segments, each suture segment having a plurality of retainers between a first and second end of the suture segment for permitting movement of the suture through tissue in a direction of movement of the first end and preventing movement of the suture through tissue in a direction opposite the direction of movement of the first end, and a grasp engagement element comprising a rigid continuous loop or polygon integrally formed with the suture segments at the second end of each suture segment;

b. positioning the grasp engagement element at least in part outside the wound;

c. inserting the first end of one of the suture segments into tissue at an insertion point at the wound; and, d. drawing the first end of the one of the suture segments towards an end of the wound along a deployment path through tissue on alternating sides of the wound to an exit point outside the tissue.

10. The method of claim 9, further comprising:

e. inserting the first end of another one of the suture segments into tissue at a second insertion point between the first and second ends of the wound, leaving a portion of the suture between the first and second insertion points;

f. drawing the first end of the another one of the suture segments towards the second end of the wound along a second deployment path through tissue on alternating sides of the wound to a second exit point; and, g. severing the suture along the portion between the first and second insertion points for removal of the suture from the wound prior to provision of permanent treatment.

11. The method of claim 10, wherein inserting the first end of the another one of the suture segments into tissue is performed before drawing the first end of the one of the suture segments towards the first end of the wound.

12. The method of claim 9, wherein said wound is a stellate wound having at least three tissue apexes, wherein said self-retaining suture is a multidirectional self-retaining suture system comprising at least three suture segments, and wherein said method further comprises:

e. inserting the first end of a second suture segment into a second tissue apex and drawing the first end of the second suture segment out of the tissue; and, f. inserting the first end of a third suture segment into tissue at a third tissue apex and drawing the first end of the third suture segment out of the tissue.

* * * * *